(12) United States Patent
Moriya et al.

(10) Patent No.: US 6,403,362 B1
(45) Date of Patent: Jun. 11, 2002

(54) SYSTEMS FOR THE MASS PRODUCTION OF PROTEINS OR PEPTIDES BY MICROORGANISMS OF THE GENUS HUMICOLA

(75) Inventors: Tatsuki Moriya, Odawara; Kouichirou Murashima, Sakado; Kaoru Aoyagi, Odawara; Naomi Sumida, Odawara; Manabu Watanabe, Odawara; Toru Hamaya, Sakado; Jinichiro Koga, Sakado; Toshiaki Kono, Sakado; Takeshi Murakami, Odawara, all of (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 0 days.

(21) Appl. No.: 09/230,225
(22) PCT Filed: Jul. 24, 1997
(86) PCT No.: PCT/JP97/02560
  § 371 (c)(1),
  (2), (4) Date: Mar. 3, 1999
(87) PCT Pub. No.: WO98/03667
  PCT Pub. Date: Jan. 29, 1998

(30) Foreign Application Priority Data

Jul. 24, 1996 (JP) .............................................. 8-195070

(51) Int. Cl.$^7$ ............................. C12N 1/14; C12N 1/16; C07K 14/00; C07K 1/00; C07K 17/00
(52) U.S. Cl. ..................... 435/254.1; 530/300; 530/326; 530/344; 530/350; 530/820; 530/823
(58) Field of Search .................................. 530/326, 344, 530/820, 823, 300, 350; 435/254.1, 320.1

(56) References Cited

FOREIGN PATENT DOCUMENTS

| | | | |
|---|---|---|---|
| EP | 0495554 A1 | * | 7/1992 |
| JP | 59-175889 | | 10/1984 |
| JP | 08-056663 | | 3/1996 |
| JP | 08-126492 | | 5/1996 |

* cited by examiner

*Primary Examiner*—Mark Navarro
(74) *Attorney, Agent, or Firm*—Varndell & Varndell, PLLC

(57) ABSTRACT

An expressing system which enables a large amount of production of a protein in Humicola, in particular, *Humicola insolens*, and particularly host-vector systems and a process for producing a protein using the systems, wherein an expression vector comprising the regulator sequences, i.e., the promoter, the signal sequence, and the terminator, of the cellulase NCE1 gene or NCE2 gene derived from *Humicola insolens* is constructed and used. The expression vector enables highly efficient production of cellulase NCE4, for example, in *Humicola insolens* at a rate as high as about 4.5 g or more per one liter of culture.

4 Claims, 5 Drawing Sheets

F I G. I

SEQUENCE LISTING

```
<160> NUMBER OF SEQ ID NOS: 34

<210> SEQ ID NO 1
<211> LENGTH: 2285
<212> TYPE: DNA
<213> ORGANISM: Humicola insolens
<220> FEATURE:
<221> NAME/KEY: sig_peptide
<222> LOCATION: (311)..(369)
<223> OTHER INFORMATION:
<221> NAME/KEY: mat_peptide
<222> LOCATION: (376)..()
<223> OTHER INFORMATION:
<221> NAME/KEY: CDS
<222> LOCATION: (376)..(879)
<223> OTHER INFORMATION:
<221> NAME/KEY: Intron
<222> LOCATION: (880)..(936)
<223> OTHER INFORMATION:
<221> NAME/KEY: CDS
<222> LOCATION: (937)..(1289)
<223> OTHER INFORMATION:
<221> NAME/KEY: Intron
<222> LOCATION: (1290)..(1348)
<223> OTHER INFORMATION:
<221> NAME/KEY: CDS
<222> LOCATION: (1349)..(1592)
<223> OTHER INFORMATION:
<221> NAME/KEY: Intron
<222> LOCATION: (1593)..(1648)
<223> OTHER INFORMATION:
<221> NAME/KEY: CDS
<222> LOCATION: (1649)..(1779)
<223> OTHER INFORMATION:
<221> NAME/KEY: Intron
<222> LOCATION: (1780)..(1835)
<223> OTHER INFORMATION:
<221> NAME/KEY: CDS
<222> LOCATION: (1836)..(1890)
<223> OTHER INFORMATION:
<221> NAME/KEY: misc_feature
<222> LOCATION: (240)..(245)
<223> OTHER INFORMATION: Cleavage site SalI
<221> NAME/KEY: misc_feature
<222> LOCATION: (603)..(608)
<223> OTHER INFORMATION: Cleavage site SalI
```

```
<221> NAME/KEY: misc_feature
<222> LOCATION: (760)..(765)
<223> OTHER INFORMATION: Cleavage site SalI
<221> NAME/KEY: misc_feature
<222> LOCATION: (1152)..(1157)
<223> OTHER INFORMATION: Cleavage site KpnI
<221> NAME/KEY: misc_feature
<222> LOCATION: (1267)..(1272)
<223> OTHER INFORMATION: Cleavage site SalI

<400> SEQUENCE: 1
tctccaataa cgacgaagcg actgttggct gatcaattag ctggcgatgg gtctgtggta      60
tggaacgtcg gctgagtctt ccatctccca ccgtagacgt gttccgcgga tcaaggtctc     120
ccgctccgta accgcccagg tggctcggtt cttgatgatg ggaaaggggc cgacggcagt     180
ataaagagcc atgaagcat ccctcgaggc cggaaggaaa tcttgctcag ccacccgcag      240
tcgacttgtc tatcgatctg agcagcagtt gaccggtctt ctctgtcatc tcagcagcag    300
tctttcaaga tgcagatcaa gagctacatc cagtacctgg ccgcggctct gccgctcctg    360
agcagcgtcg ctgcc cag cag gcc ggc acc atc acc gcc gag aac cac ccc     411
              Gln Gln Ala Gly Thr Ile Thr Ala Glu Asn His Pro
                1           5                  10 agg atg acc tgg aag agg tgc tcg ggc ccc ggc aac tgc cag acc gtg     459
Arg Met Thr Trp Lys Arg Cys Ser Gly Pro Gly Asn Cys Gln Thr Val
         15                  20                  25 cag ggc gag gtc gtc atc gac gcc aac tgg cgc tgg ctg cac aac aac     507
Gln Gly Glu Val Val Ile Asp Ala Asn Trp Arg Trp Leu His Asn Asn
 30                  35                  40 ggc cag aac tgc tat gag ggc aac aag tgg acc agc cag tgc agc tcg     555
Gly Gln Asn Cys Tyr Glu Gly Asn Lys Trp Thr Ser Gln Cys Ser Ser
45                  50                  55                  60 gcc acc gac tgc gcg cag agg tgc gcc ctc gac ggt gcc aac tac cag     603
Ala Thr Asp Cys Ala Gln Arg Cys Ala Leu Asp Gly Ala Asn Tyr Gln
                 65                  70                  75 tcg acc tac ggc gcc tcg acc agc ggc gac tcc ctg acg ctc aag ttc     651
Ser Thr Tyr Gly Ala Ser Thr Ser Gly Asp Ser Leu Thr Leu Lys Phe
             80                  85                  90 gtc acc aag cac gag tac ggc acc aac atc ggc tcg cgc ttc tac ctc     699
Val Thr Lys His Glu Tyr Gly Thr Asn Ile Gly Ser Arg Phe Tyr Leu
         95                  100                 105 atg gcc aac cag aac aag tac cag atg ttc acc ctg atg aac aac gag     747
Met Ala Asn Gln Asn Lys Tyr Gln Met Phe Thr Leu Met Asn Asn Glu
     110                 115                 120 ttc gcc ttc gat gtc gac ctc tcc aag gtt gag tgc ggt atc aac agc     795
Phe Ala Phe Asp Val Asp Leu Ser Lys Val Glu Cys Gly Ile Asn Ser
125                 130                 135                 140 gct ctg tac ttc gtc gcc atg gag gag gat ggt ggc atg gcc agc tac     843
Ala Leu Tyr Phe Val Ala Met Glu Glu Asp Gly Gly Met Ala Ser Tyr
                 145                 150                 155 ccg agc aac cgt gct ggt gcc aag tac ggc acg ggc gtacgttctc           889
Pro Ser Asn Arg Ala Gly Ala Lys Tyr Gly Thr Gly
             160                 165 tccgtcccgc ccctaccaaa agtatgactc gtgctgacgt ttgacag tac tgc gat     945
                                                    Tyr Cys Asp
                                                            170 gcc caa tgc gcc cgt gac ctc aag ttc att ggc ggc aag gcc aac att     993
Ala Gln Cys Ala Arg Asp Leu Lys Phe Ile Gly Gly Lys Ala Asn Ile
             175                 180                 185 gag ggc tgg cgc ccg tcc acc aac gac ccc aac gcc ggt gtc ggt ccc    1041
Glu Gly Trp Arg Pro Ser Thr Asn Asp Pro Asn Ala Gly Val Gly Pro
     190                 195                 200
```

```
atg ggt gcc tgc tgc gct gag atc gac gtt tgg gag tcc aac gcc tat     1089
Met Gly Ala Cys Cys Ala Glu Ile Asp Val Trp Glu Ser Asn Ala Tyr
    205                 210                 215 gct tat gcc ttc acc ccc cac gcc tgc ggc agc aag aac cgc tac cac     1137
Ala Tyr Ala Phe Thr Pro His Ala Cys Gly Ser Lys Asn Arg Tyr His
220                 225                 230                 235 atc tgc gag acc aac aac tgc ggt ggt acc tac tcg gat gac cgc ttc     1185
Ile Cys Glu Thr Asn Asn Cys Gly Gly Thr Tyr Ser Asp Asp Arg Phe
                240                 245                 250 gcc ggc tac tgc gac gcc aac ggc tgc gac tac aac ccc tac cgc atg     1233
Ala Gly Tyr Cys Asp Ala Asn Gly Cys Asp Tyr Asn Pro Tyr Arg Met
            255                 260                 265 ggc aac aag gac ttc tat ggc aag ggc aag acc gtc gac acc aac cgc     1281
Gly Asn Lys Asp Phe Tyr Gly Lys Gly Lys Thr Val Asp Thr Asn Arg
        270                 275                 280 aag ttc ac  gtaagttccc tggccgcctc ttcgacgacg cagaatgtcc             1329
Lys Phe Thr
    285 ggatgctgac ccagaacag c gtt gtc tcc cgc ttc gag cgt aac agg ctc      1379
                      Val Val Ser Arg Phe Glu Arg Asn Arg Leu
                                      290                 295 tct cag ttc ttc gtc cag gac ggc cgc aag atc gag gtg ccc cct ccg     1427
Ser Gln Phe Phe Val Gln Asp Gly Arg Lys Ile Glu Val Pro Pro Pro
            300                 305                 310 acc tgg ccc ggc ctc ccg aac agc gcc gac atc acc cct gag ctc tgc     1475
Thr Trp Pro Gly Leu Pro Asn Ser Ala Asp Ile Thr Pro Glu Leu Cys
        315                 320                 325 gat gct cag ttc cgc gtc ttc gat gac cgc aac cgc ttc gcc gag acc     1523
Asp Ala Gln Phe Arg Val Phe Asp Asp Arg Asn Arg Phe Ala Glu Thr
    330                 335                 340 ggt ggc ttc gat gct ctg aac gag gcc ctc acc att ccc atg gtc ctt     1571
Gly Gly Phe Asp Ala Leu Asn Glu Ala Leu Thr Ile Pro Met Val Leu
345                 350                 355                 360 gtc atg tcc atc tgg gat gac gtatgtggca ccaacctcca accgggcatg        1622
Val Met Ser Ile Trp Asp Asp
                365 agacctgtac tgacgtgtct tgacag cac cac tcc aac atg ctc tgg ctc gac   1675
                              His His Ser Asn Met Leu Trp Leu Asp
                                              370                 375 tcc agc tac ccg ccc gag aag gcc ggc ctc ccc ggt ggc gac cgt ggc     1723
Ser Ser Tyr Pro Pro Glu Lys Ala Gly Leu Pro Gly Gly Asp Arg Gly
            380                 385                 390 ccg tgc ccg acc acc tct ggt gtc cct gcc gag gtc gag gct cag tac     1771
Pro Cys Pro Thr Thr Ser Gly Val Pro Ala Glu Val Glu Ala Gln Tyr
        395                 400                 405 ccc aat gc  gtacgttact accgccgctg catctgcaaa aaataccggt             1819
Pro Asn Ala
    410 gctaaccatt gtgcag t cag gtc gtc tgg tcc aac atc cgc ttc ggc ccc     1869
                    Gln Val Val Trp Ser Asn Ile Arg Phe Gly Pro
                                    415                 420 atc ggc tcg acc gtc aac gtc taagctatca cggctcaaaa tcagcgcccg        1920
Ile Gly Ser Thr Val Asn Val
                425 ctctgctcgt cctgttcggc gcgccagtag ggggatatgg ggcatttctt tgttcaagca   1980 tttttctctt cgtcctgcta catattgaga ttgtgtatcg tatgcacgcg tacaaagtag   2040 aaaccatgat caagtctcat tgaactatac tgctgctccc aagattaatt atgccgtaat   2100
```

```
ggtctgtttg cttttttttt tttttttttt tggtgcactt gatcgtgtgg cacattggcc   2160
gctgtatgta tggcttccct caatcgccga ctgactcaaa acggcagtac aacagaagcc   2220
ccattgcatc agaagagagg ttttataatg ccatgaggtg ttctcagatg aaagacttcg   2280
agtat                                                                2285
```

```
<210> SEQ ID NO 2
<211> LENGTH: 429
<212> TYPE: PRT
<213> ORGANISM: Humicola insolens
<220> FEATURE:
<221> NAME/KEY: misc_feature
<222> LOCATION: (240)..(245)
<223> OTHER INFORMATION: Cleavage site SalI
<221> NAME/KEY: misc_feature
<222> LOCATION: (603)..(608)
<223> OTHER INFORMATION: Cleavage site SalI
<221> NAME/KEY: misc_feature
<222> LOCATION: (760)..(765)
<223> OTHER INFORMATION: Cleavage site SalI
<221> NAME/KEY: misc_feature
<222> LOCATION: (1152)..(1157)
<223> OTHER INFORMATION: Cleavage site KpnI
<221> NAME/KEY: misc_feature
<222> LOCATION: (1267)..(1272)
<223> OTHER INFORMATION: Cleavage site SalI

<400> SEQUENCE: 2

Gln Gln Ala Gly Thr Ile Thr Ala Glu Asn His Pro Arg Met Thr Trp
1               5                   10                  15

Lys Arg Cys Ser Gly Pro Gly Asn Cys Gln Thr Val Gln Gly Glu Val
            20                  25                  30

Val Ile Asp Ala Asn Trp Arg Trp Leu His Asn Asn Gly Gln Asn Cys
        35                  40                  45

Tyr Glu Gly Asn Lys Trp Thr Ser Gln Cys Ser Ser Ala Thr Asp Cys
    50                  55                  60

Ala Gln Arg Cys Ala Leu Asp Gly Ala Asn Tyr Gln Ser Thr Tyr Gly
65                  70                  75                  80

Ala Ser Thr Ser Gly Asp Ser Leu Thr Leu Lys Phe Val Thr Lys His
                85                  90                  95

Glu Tyr Gly Thr Asn Ile Gly Ser Arg Phe Tyr Leu Met Ala Asn Gln
            100                 105                 110

Asn Lys Tyr Gln Met Phe Thr Leu Met Asn Asn Glu Phe Ala Phe Asp
        115                 120                 125

Val Asp Leu Ser Lys Val Glu Cys Gly Ile Asn Ser Ala Leu Tyr Phe
    130                 135                 140

Val Ala Met Glu Glu Asp Gly Gly Met Ala Ser Tyr Pro Ser Asn Arg
145                 150                 155                 160

Ala Gly Ala Lys Tyr Gly Thr Gly Tyr Cys Asp Ala Gln Cys Ala Arg
                165                 170                 175

Asp Leu Lys Phe Ile Gly Gly Lys Ala Asn Ile Glu Gly Trp Arg Pro
            180                 185                 190

Ser Thr Asn Asp Pro Asn Ala Gly Val Gly Pro Met Gly Ala Cys Cys
        195                 200                 205

Ala Glu Ile Asp Val Trp Glu Ser Asn Ala Tyr Ala Tyr Ala Phe Thr
    210                 215                 220

Pro His Ala Cys Gly Ser Lys Asn Arg Tyr His Ile Cys Glu Thr Asn
225                 230                 235                 240

Asn Cys Gly Gly Thr Tyr Ser Asp Asp Arg Phe Ala Gly Tyr Cys Asp
                245                 250                 255
```

```
            Ala Asn Gly Cys Asp Tyr Asn Pro Tyr Arg Met Gly Asn Lys Asp Phe
                        260                 265                 270

Tyr Gly Lys Gly Lys Thr Val Asp Thr Asn Arg Lys Phe Thr Val Val
                        275                 280                 285

Ser Arg Phe Glu Arg Asn Arg Leu Ser Gln Phe Phe Val Gln Asp Gly
                        290                 295                 300

Arg Lys Ile Glu Val Pro Pro Thr Trp Pro Gly Leu Pro Asn Ser
            305                 310                 315                 320

Ala Asp Ile Thr Pro Glu Leu Cys Asp Ala Gln Phe Arg Val Phe Asp
                        325                 330                 335

Asp Arg Asn Arg Phe Ala Glu Thr Gly Gly Phe Asp Ala Leu Asn Glu
                        340                 345                 350

Ala Leu Thr Ile Pro Met Val Leu Val Met Ser Ile Trp Asp Asp His
                        355                 360                 365

His Ser Asn Met Leu Trp Leu Asp Ser Ser Tyr Pro Pro Glu Lys Ala
                        370                 375                 380

Gly Leu Pro Gly Gly Asp Arg Gly Pro Cys Pro Thr Thr Ser Gly Val
            385                 390                 395                 400

Pro Ala Glu Val Glu Ala Gln Tyr Pro Asn Ala Gln Val Val Trp Ser
                        405                 410                 415

Asn Ile Arg Phe Gly Pro Ile Gly Ser Thr Val Asn Val
                        420                 425

<210> SEQ ID NO 3
<211> LENGTH: 2409
<212> TYPE: DNA
<213> ORGANISM: Humicola insolens
<220> FEATURE:
<221> NAME/KEY: sig_peptide
<222> LOCATION: (389)..(457)
<223> OTHER INFORMATION:
<221> NAME/KEY: mat_peptide
<222> LOCATION: (458)..()
<223> OTHER INFORMATION:
<221> NAME/KEY: CDS
<222> LOCATION: (458)..(477)
<223> OTHER INFORMATION:
<221> NAME/KEY: Intron
<222> LOCATION: (478)..(535)
<223> OTHER INFORMATION:
<221> NAME/KEY: CDS
<222> LOCATION: (536)..(1029)
<223> OTHER INFORMATION:
<221> NAME/KEY: Intron
<222> LOCATION: (1030)..(1141)
<223> OTHER INFORMATION:
<221> NAME/KEY: CDS
<222> LOCATION: (1142)..(1761)
<223> OTHER INFORMATION:
<221> NAME/KEY: Intron
<222> LOCATION: (1762)..(1815)
<223> OTHER INFORMATION:
<221> NAME/KEY: CDS
<222> LOCATION: (1816)..(1989)
<223> OTHER INFORMATION:
<221> NAME/KEY: Intron
<222> LOCATION: (1990)..(2044)
<223> OTHER INFORMATION:
<221> NAME/KEY: CDS
<222> LOCATION: (2045)..(2095)
<223> OTHER INFORMATION:
<221> NAME/KEY: misc_feature
<222> LOCATION: (688)..(693)
<223> OTHER INFORMATION: Cleavage site SmaI
<221> NAME/KEY: misc_feature
<222> LOCATION: (1253)..(1259)
<223> OTHER INFORMATION: Cleavage site BamH1
```

```
<221> NAME/KEY: misc_feature
<222> LOCATION: (1505)..(1510)
<223> OTHER INFORMATION: Cleavage site BglII
<221> NAME/KEY: misc_feature
<222> LOCATION: (1643)..(1648)
<223> OTHER INFORMATION: Cleavage siteStuI

<400> SEQUENCE: 3
```

| | | | | | |
|---|---|---|---|---|---|
| tgctggacct | tggatgcgtc | tgccgagctg | tgcgtgcgga | agagtcgagc | gtgattccgg | 60 |
| catcactgaa | cactcgctgg | ttgctggttc | tggaagcggt | acgtccggcg | caaaccagca | 120 |
| aaagcaggtt | tgcgctgcct | tggcctccgt | gagaggcatg | atgccaagga | tgaatggttc | 180 |
| ctctgcggac | tcaaccatcc | gcacttcgag | cccgacgatc | cgggcccct | gctccggcgc | 240 |
| ggagagccgt | ggtgagctcc | aagtgatgcg | gaatcggtga | tgtgcaagat | gcggagggca | 300 |
| taaaaaggct | gtttcccaca | cgaagcattc | tccagcttgt | ttcctcacgg | cacacggtca | 360 |
| aacaagtctg | tgcagtacct | gggacaagat | ggccaagttc | ttccttactg | ctgcctttgc | 420 |
| ggctgccgct | ctcgccgctc | ccgttgttga | ggagcgc cag aac tgt gcc ccg act | | | 475 |

```
                                         Gln Asn Cys Ala Pro Thr
                                          1               5
```

| | |
|---|---|
| tg gtgagcaatg gtgtttcatg gatcgtgtct ttggatgtgc ggctaacaac | 527 |
| Trp | |

```
cattccag g ggc cag tgc ggt ggc atc ggc ttc aat ggc ccg act tgc     575
           Gly Gln Cys Gly Gly Ile Gly Phe Asn Gly Pro Thr Cys
            10               15              20 tgc cag tct ggt agc acc tgc gtg aag cag aac gac tgg tac tcc cag     623
Cys Gln Ser Gly Ser Thr Cys Val Lys Gln Asn Asp Trp Tyr Ser Gln
             25                  30                  35 tgc ttg ccc ggt agc cag gtc acc acg acc tcg act acg tcg act tcg     671
Cys Leu Pro Gly Ser Gln Val Thr Thr Thr Ser Thr Thr Ser Thr Ser
         40                  45                  50 agc tcg tcg acc acc tcc cgg gcc acc tcg acc acc agg acc ggt ggt     719
Ser Ser Ser Thr Thr Ser Arg Ala Thr Ser Thr Thr Arg Thr Gly Gly
     55                  60                  65 gtg acc tcg atc acc act gct ccc acc cgc acc gtc acc atc cct ggc     767
Val Thr Ser Ile Thr Thr Ala Pro Thr Arg Thr Val Thr Ile Pro Gly
 70                  75                  80 ggt gcc acc acg acg gcc agc tac aac ggc aac ccc ttc gag ggt gtc     815
Gly Ala Thr Thr Thr Ala Ser Tyr Asn Gly Asn Pro Phe Glu Gly Val
85                  90                  95                 100 cag ctc tgg gcc aac aac tac tac cgc tct gag gtc cac acc ctc gcc     863
Gln Leu Trp Ala Asn Asn Tyr Tyr Arg Ser Glu Val His Thr Leu Ala
                105                 110                 115 att cct cag atc acc gac cct gcc ttg agg gct gcg gcc tcg gcc gtc     911
Ile Pro Gln Ile Thr Asp Pro Ala Leu Arg Ala Ala Ala Ser Ala Val
            120                 125                 130 gct gag gtc ccg agc ttc cag tgg ctc gac cgc aac gtc acg gtc gac     959
Ala Glu Val Pro Ser Phe Gln Trp Leu Asp Arg Asn Val Thr Val Asp
        135                 140                 145 acc ctg ctc gtc gag acc ctc tct gag atc cgc gcc gcg aac cag gcg    1007
Thr Leu Leu Val Glu Thr Leu Ser Glu Ile Arg Ala Ala Asn Gln Ala
    150                 155                 160 ggc gcg aac ccc ccg tat gcc g gtaagtgcgg tgtcaccacc accaaccta      1059
Gly Ala Asn Pro Pro Tyr Ala
165                 170
```

| | |
|---|---|
| accctgaccc ctgaccacca catcatcaac atcaccacac atctcccaca tcattctgga | 1119 |
| cgcaaattaa cgccaaatcc ag cc cag atc gtc gtt tac gac ctt cct gac | 1170 |

```
                              Ala Gln Ile Val Val Tyr Asp Leu Pro Asp
                                  175                 180
```

```
cgc gac tgc gct gcc gcg gct tcg aac ggc gag tgg gcg atc gcc aac       1218
Arg Asp Cys Ala Ala Ala Ser Asn Gly Glu Trp Ala Ile Ala Asn
            185                 190                 195 aac ggc gcc aac aac tac aag gga tac atc aac cgg atc cgc gag att       1266
Asn Gly Ala Asn Asn Tyr Lys Gly Tyr Ile Asn Arg Ile Arg Glu Ile
                200                 205                 210 ctc att tcg ttc tcg gat gtc cgc acg att ctg gtt atc gag ccc gac       1314
Leu Ile Ser Phe Ser Asp Val Arg Thr Ile Leu Val Ile Glu Pro Asp
            215                 220                 225 tcg ctg gcc aac atg gtc acc aac atg aac gtc gcc aag tgc agc ggt       1362
Ser Leu Ala Asn Met Val Thr Asn Met Asn Val Ala Lys Cys Ser Gly
230                 235                 240                 245 gcc gcc tcg acc tac cgc gag ttg acc atc tat gcc ctc aag cag ctc       1410
Ala Ala Ser Thr Tyr Arg Glu Leu Thr Ile Tyr Ala Leu Lys Gln Leu
                250                 255                 260 gac ctc ccg cac gtc gcc atg tac atg gac gcc ggc cac gct ggc tgg       1458
Asp Leu Pro His Val Ala Met Tyr Met Asp Ala Gly His Ala Gly Trp
            265                 270                 275 ctt ggc tgg ccc gcc aac atc cag ccc gct gct gag ctc ttc gcc aag       1506
Leu Gly Trp Pro Ala Asn Ile Gln Pro Ala Ala Glu Leu Phe Ala Lys
            280                 285                 290 atc tac gag gat gcc ggc aag ccc cgc gcc gtc cgc ggt ctc gcc acc       1554
Ile Tyr Glu Asp Ala Gly Lys Pro Arg Ala Val Arg Gly Leu Ala Thr
295                 300                 305 aac gtc gcc aac tac aac gcc tgg agc atc tcg agc ccg ccg ccg tac       1602
Asn Val Ala Asn Tyr Asn Ala Trp Ser Ile Ser Ser Pro Pro Pro Tyr
310                 315                 320                 325 acc agc ccc aac ccc aac tac gac gag aag cac tac atc gag gcc ttc       1650
Thr Ser Pro Asn Pro Asn Tyr Asp Glu Lys His Tyr Ile Glu Ala Phe
                330                 335                 340 cgc cct ctc ctc gag gcc cgc ggc ttc ccc gcc cag ttc atc gtc gac       1698
Arg Pro Leu Leu Glu Ala Arg Gly Phe Pro Ala Gln Phe Ile Val Asp
            345                 350                 355 cag ggc cgc agc ggc aag cag ccc acc ggc cag aag gaa tgg ggc cac       1746
Gln Gly Arg Ser Gly Lys Gln Pro Thr Gly Gln Lys Glu Trp Gly His
            360                 365                 370 tgg tgc aat gcc att gtacgttaag gttagggtta catatttgcg ttcccatgac       1801
Trp Cys Asn Ala Ile
    375 taacatcctt ccag ggc acc ggc ttc ggt atg cgc ccg act gcc aac acc       1851
               Gly Thr Gly Phe Gly Met Arg Pro Thr Ala Asn Thr
               380                 385                 390 ggc cac cag tac gtc gac gcc ttc gtc tgg gtc aag ccc ggc ggt gag       1899
Gly His Gln Tyr Val Asp Ala Phe Val Trp Val Lys Pro Gly Gly Glu
                395                 400                 405 tgc gac ggc acc agc gac acg acc gct gcc cgc tac gac tac cac tgc       1947
Cys Asp Gly Thr Ser Asp Thr Thr Ala Ala Arg Tyr Asp Tyr His Cys
            410                 415                 420 ggt ctc gag gac gcc ctc aag ccc gcc cct gag gcc ggc cag                1989
Gly Leu Glu Asp Ala Leu Lys Pro Ala Pro Glu Ala Gly Gln
            425                 430                 435 gtgagcacca aacccgacca caacaagaaa tgtaccaaag gctaaccaac tccag tgg       2047
                                                              Trp ttc caa gcc tac ttt gag caa tta ctt cgt aat gcc aat ccg ccg ttc       2095
Phe Gln Ala Tyr Phe Glu Gln Leu Leu Arg Asn Ala Asn Pro Pro Phe
            440                 445                 450 tgagcggttt gaggcgtttg gcgcgatgtt ggcgatgttt aggatcaaaa aggggggaa      2155 aaggcgaaaa ggggccggtc cgggaggccc cacaatatcg gccccaccct ccgatcacgt     2215
```

-continued

```
gctccccgca tcggcacaga cgtcgcttaa tgcattgagg gggttgacaa aattcaagtc    2275
ttcttctgta aatagttggc atctgccatt gttggacaag atttagtctt tcgagtatat    2335
acactttgtt ccaacggggt ctagtaactt ccgaggtcat ctcatcaagc attgtttgag    2395
tctcgcgttt atac                                                      2409
```

<210> SEQ ID NO 4
<211> LENGTH: 453
<212> TYPE: PRT
<213> ORGANISM: Humicola insolens
<220> FEATURE:
<221> NAME/KEY: misc_feature
<222> LOCATION: (688)..(693)
<223> OTHER INFORMATION: Cleavage site SmaI
<221> NAME/KEY: misc_feature
<222> LOCATION: (1253)..(1259)
<223> OTHER INFORMATION: Cleavage site BamH1
<221> NAME/KEY: misc_feature
<222> LOCATION: (1505)..(1510)
<223> OTHER INFORMATION: Cleavage site BglII
<221> NAME/KEY: misc_feature
<222> LOCATION: (1643)..(1648)
<223> OTHER INFORMATION: Cleavage siteStuI

<400> SEQUENCE: 4

```
Gln Asn Cys Ala Pro Thr Trp Gly Gln Cys Gly Gly Ile Gly Phe Asn
 1               5                  10                  15

Gly Pro Thr Cys Cys Gln Ser Gly Ser Thr Cys Val Lys Gln Asn Asp
                20                  25                  30

Trp Tyr Ser Gln Cys Leu Pro Gly Ser Gln Val Thr Thr Thr Ser Thr
            35                  40                  45

Thr Ser Thr Ser Ser Ser Ser Thr Ser Arg Ala Thr Ser Thr Thr
    50                  55                  60

Arg Thr Gly Gly Val Thr Ser Ile Thr Thr Ala Pro Thr Arg Thr Val
65                  70                  75                  80

Thr Ile Pro Gly Gly Ala Thr Thr Thr Ala Ser Tyr Asn Gly Asn Pro
                85                  90                  95

Phe Glu Gly Val Gln Leu Trp Ala Asn Asn Tyr Tyr Arg Ser Glu Val
               100                 105                 110

His Thr Leu Ala Ile Pro Gln Ile Thr Asp Pro Ala Leu Arg Ala Ala
           115                 120                 125

Ala Ser Ala Val Ala Glu Val Pro Ser Phe Gln Trp Leu Asp Arg Asn
130                 135                 140

Val Thr Val Asp Thr Leu Leu Val Glu Thr Leu Ser Glu Ile Arg Ala
145                 150                 155                 160

Ala Asn Gln Ala Gly Ala Asn Pro Pro Tyr Ala Ala Gln Ile Val Val
                165                 170                 175

Tyr Asp Leu Pro Asp Arg Asp Cys Ala Ala Ala Ser Asn Gly Glu
            180                 185                 190

Trp Ala Ile Ala Asn Asn Gly Ala Asn Asn Tyr Lys Gly Tyr Ile Asn
        195                 200                 205

Arg Ile Arg Glu Ile Leu Ile Ser Phe Ser Asp Val Arg Thr Ile Leu
    210                 215                 220

Val Ile Glu Pro Asp Ser Leu Ala Asn Met Val Thr Asn Met Asn Val
225                 230                 235                 240

Ala Lys Cys Ser Gly Ala Ala Ser Thr Tyr Arg Glu Leu Thr Ile Tyr
                245                 250                 255

Ala Leu Lys Gln Leu Asp Leu Pro His Val Ala Met Tyr Met Asp Ala
```

-continued

```
                    260                 265                 270
Gly His Ala Gly Trp Leu Gly Trp Pro Ala Asn Ile Gln Pro Ala Ala
            275                 280                 285
Glu Leu Phe Ala Lys Ile Tyr Glu Asp Ala Gly Lys Pro Arg Ala Val
        290                 295                 300
Arg Gly Leu Ala Thr Asn Val Ala Asn Tyr Asn Ala Trp Ser Ile Ser
305                 310                 315                 320
Ser Pro Pro Pro Tyr Thr Ser Pro Asn Pro Asn Tyr Asp Glu Lys His
                325                 330                 335
Tyr Ile Glu Ala Phe Arg Pro Leu Leu Glu Ala Arg Gly Phe Pro Ala
            340                 345                 350
Gln Phe Ile Val Asp Gln Gly Arg Ser Gly Lys Gln Pro Thr Gly Gln
        355                 360                 365
Lys Glu Trp Gly His Trp Cys Asn Ala Ile Gly Thr Gly Phe Gly Met
    370                 375                 380
Arg Pro Thr Ala Asn Thr Gly His Gln Tyr Val Asp Ala Phe Val Trp
385                 390                 395                 400
Val Lys Pro Gly Gly Glu Cys Asp Gly Thr Ser Asp Thr Thr Ala Ala
                405                 410                 415
Arg Tyr Asp Tyr His Cys Gly Leu Glu Asp Ala Leu Lys Pro Ala Pro
            420                 425                 430
Glu Ala Gly Gln Trp Phe Gln Ala Tyr Phe Glu Gln Leu Leu Arg Asn
        435                 440                 445
Ala Asn Pro Pro Phe
    450
```

```
<210> SEQ ID NO 5
<211> LENGTH: 1257
<212> TYPE: DNA
<213> ORGANISM: Humicola insolens
<220> FEATURE:
<221> NAME/KEY: sig_peptide
<222> LOCATION: (118)..(180)
<223> OTHER INFORMATION:
<221> NAME/KEY: mat_peptide
<222> LOCATION: (181)..()
<223> OTHER INFORMATION:
<221> NAME/KEY: CDS
<222> LOCATION: (178)..(452)
<223> OTHER INFORMATION:
<221> NAME/KEY: Intron
<222> LOCATION: (453)..(508)
<223> OTHER INFORMATION:
<221> NAME/KEY: CDS
<222> LOCATION: (509)..(1088)
<223> OTHER INFORMATION:

<400> SEQUENCE: 5
aatgacgggg caacctcccg cccgggccca actcttgggt ttggtttgac aggccgtctg      60
tctcttgcgt cctcttacta cgcctgcctg gaccctacgt ctcaactccg attcaagatg    120
cgttcctccc ctctcctccg ctccgccgtt gtggccgccg tccggtgtt ggcccctt       177 gcc gct gat ggc aag tcc acc cgc tac tgg gac tgc tgc aag cct tcg     225
Ala Ala Asp Gly Lys Ser Thr Arg Tyr Trp Asp Cys Cys Lys Pro Ser
 -1   1               5                  10                  15 tgc ggc tgg gcc aag aag gct ccc gtg aac cag cct gtc ttc tcc tgc     273
Cys Gly Trp Ala Lys Lys Ala Pro Val Asn Gln Pro Val Phe Ser Cys
             20                  25                  30 aac gcc aac ttc cag cgt ctc act gac ttc gac gcc aag tcc ggc tgc     321
Asn Ala Asn Phe Gln Arg Leu Thr Asp Phe Asp Ala Lys Ser Gly Cys
         35                  40                  45
```

```
gag ccg ggc ggt gtc gcc tac tcg tgc gcc gac cag acc cca tgg gct      369
Glu Pro Gly Gly Val Ala Tyr Ser Cys Ala Asp Gln Thr Pro Trp Ala
         50                  55                  60 gtg aac gac gac ttc gcg ttc ggt ttt gct gcc acc tct att gcc ggc      417
Val Asn Asp Asp Phe Ala Phe Gly Phe Ala Ala Thr Ser Ile Ala Gly
 65                  70                  75 agc aat gag gcg ggc tgg tgc tgc gcc tgc tac ga gtaagctttg            462
Ser Asn Glu Ala Gly Trp Cys Cys Ala Cys Tyr Glu
 80                  85                  90 gtcgcgtgtg taacactgtg caggcatagc actaaccacc tcccag g ctc acc ttc     518
                                                   Leu Thr Phe aca tcc ggt cct gtt gct ggc aag aag atg gtc gtc cag tcc acc agc      566
Thr Ser Gly Pro Val Ala Gly Lys Lys Met Val Val Gln Ser Thr Ser
 95                 100                 105                 110 act ggt ggt gat ctt ggc agc aac cac ttc gat ctc aac atc ccc ggc      614
Thr Gly Gly Asp Leu Gly Ser Asn His Phe Asp Leu Asn Ile Pro Gly
                115                 120                 125 ggc ggc gtc ggc atc ttc gac gga tgc act ccc cag ttc ggc ggt ctg      662
Gly Gly Val Gly Ile Phe Asp Gly Cys Thr Pro Gln Phe Gly Gly Leu
            130                 135                 140 ccc ggc cag cgc tac ggc ggc atc tcg tcc cgc aac gag tgc gat cgg      710
Pro Gly Gln Arg Tyr Gly Gly Ile Ser Ser Arg Asn Glu Cys Asp Arg
        145                 150                 155 ttc ccc gac gcc ctc aag ccc ggc tgc tac tgg cgc ttc gac tgg ttc      758
Phe Pro Asp Ala Leu Lys Pro Gly Cys Tyr Trp Arg Phe Asp Trp Phe
    160                 165                 170 aag aac gcc gac aac ccg agc ttc agc ttc cgt cag gtc caa tgc cca      806
Lys Asn Ala Asp Asn Pro Ser Phe Ser Phe Arg Gln Val Gln Cys Pro
175                 180                 185                 190 gcc gag ctc gtc gct cgc acc gga tgc cgc cgc aac gac gac ggc aac      854
Ala Glu Leu Val Ala Arg Thr Gly Cys Arg Arg Asn Asp Asp Gly Asn
                195                 200                 205 ttc cct gcc gtc cag atc ccc tcc agc agc acc agc tct ccg gtc ggc      902
Phe Pro Ala Val Gln Ile Pro Ser Ser Ser Thr Ser Ser Pro Val Gly
            210                 215                 220 cag cct acc agt acc agc acc acc tcc acc tcc acc acc tcg agc ccg      950
Gln Pro Thr Ser Thr Ser Thr Thr Ser Thr Ser Thr Thr Ser Ser Pro
        225                 230                 235 ccc gtc cag cct acg act ccc agc ggc tgc act gct gag agg tgg gct      998
Pro Val Gln Pro Thr Thr Pro Ser Gly Cys Thr Ala Glu Arg Trp Ala
    240                 245                 250 cag tgc ggc ggc aat ggc tgg agc ggc tgc acc acc tgc gtc gct ggc     1046
Gln Cys Gly Gly Asn Gly Trp Ser Gly Cys Thr Thr Cys Val Ala Gly
255                 260                 265                 270 agc acc tgc acg aag att aat gac tgg tac cat cag tgc ctg             1088
Ser Thr Cys Thr Lys Ile Asn Asp Trp Tyr His Gln Cys Leu
                275                 280 taaacgcagg gcagcctgag aaccttactg gttgcgcaac gaaatgacac tcccaatcac   1148
tgtattagtt cttgtacata atttcgtcat ccctccaggg attgtcacat atatgcaatg   1208
atgaatactg aacacaaacc tggccgcttg aactggccga aggaatgcc              1257

<210> SEQ ID NO 6
<211> LENGTH: 285
<212> TYPE: PRT
<213> ORGANISM: Humicola insolens

<400> SEQUENCE: 6

Ala Ala Asp Gly Lys Ser Thr Arg Tyr Trp Asp Cys Cys Lys Pro Ser
```

```
              -1   1                   5                        10                         15
              Cys  Gly  Trp  Ala  Lys  Lys  Ala  Pro  Val  Asn  Gln  Pro  Val  Phe  Ser  Cys
                             20                        25                       30

Asn  Ala  Asn  Phe  Gln  Arg  Leu  Thr  Asp  Phe  Asp  Ala  Lys  Ser  Gly  Cys
                             35                        40                       45

Glu  Pro  Gly  Gly  Val  Ala  Tyr  Ser  Cys  Ala  Asp  Gln  Thr  Pro  Trp  Ala
                             50                        55                       60

Val  Asn  Asp  Asp  Phe  Ala  Phe  Gly  Phe  Ala  Ala  Thr  Ser  Ile  Ala  Gly
                             65                        70                       75

Ser  Asn  Glu  Ala  Gly  Trp  Cys  Cys  Ala  Cys  Tyr  Glu  Leu  Thr  Phe  Thr
              80                       85                        90                       95

Ser  Gly  Pro  Val  Ala  Gly  Lys  Lys  Met  Val  Val  Gln  Ser  Thr  Ser  Thr
                            100                       105                      110

Gly  Gly  Asp  Leu  Gly  Ser  Asn  His  Phe  Asp  Leu  Asn  Ile  Pro  Gly  Gly
                            115                       120                      125

Gly  Val  Gly  Ile  Phe  Asp  Gly  Cys  Thr  Pro  Gln  Phe  Gly  Gly  Leu  Pro
                            130                       135                      140

Gly  Gln  Arg  Tyr  Gly  Gly  Ile  Ser  Ser  Arg  Asn  Glu  Cys  Asp  Arg  Phe
                            145                       150                      155

Pro  Asp  Ala  Leu  Lys  Pro  Gly  Cys  Tyr  Trp  Arg  Phe  Asp  Trp  Phe  Lys
              160                      165                       170                      175

Asn  Ala  Asp  Asn  Pro  Ser  Phe  Ser  Phe  Arg  Gln  Val  Gln  Cys  Pro  Ala
                            180                       185                      190

Glu  Leu  Val  Ala  Arg  Thr  Gly  Cys  Arg  Arg  Asn  Asp  Asp  Gly  Asn  Phe
                            195                       200                      205

Pro  Ala  Val  Gln  Ile  Pro  Ser  Ser  Ser  Thr  Ser  Ser  Pro  Val  Gly  Gln
                            210                       215                      220

Pro  Thr  Ser  Thr  Ser  Thr  Thr  Ser  Thr  Ser  Thr  Thr  Ser  Ser  Pro  Pro
                            225                       230                      235

Val  Gln  Pro  Thr  Thr  Pro  Ser  Gly  Cys  Thr  Ala  Glu  Arg  Trp  Ala  Gln
              240                      245                       250                      255

Cys  Gly  Gly  Asn  Gly  Trp  Ser  Gly  Cys  Thr  Thr  Cys  Val  Ala  Gly  Ser
                            260                       265                      270

Thr  Cys  Thr  Lys  Ile  Asn  Asp  Trp  Tyr  His  Gln  Cys  Leu
                            275                       280

<210> SEQ ID NO 7
<211> LENGTH: 16
<212> TYPE: PRT
<213> ORGANISM: Humicola insolens

<400> SEQUENCE: 7

Gln  Asn  Cys  Gly  Ser  Leu  Thr  Thr  Glu  Arg  His  Pro  Ser  Leu  Ser  Trp
1                  5                        10                       15

<210> SEQ ID NO 8
<211> LENGTH: 20
<212> TYPE: PRT
<213> ORGANISM: Humicola insolens

<400> SEQUENCE: 8

Val  Val  Glu  Glu  Arg  Gln  Asn  Cys  Gly  Ser  Ala  Asp  Gly  Lys  Ser  Thr
1                  5                        10                       15

Arg  Tyr  Trp  Asp
                  20
```

```
<210> SEQ ID NO 9
<211> LENGTH: 21
<212> TYPE: PRT
<213> ORGANISM: Humicola insolens

<400> SEQUENCE: 9

Gln Asn Cys Gly Ser Ala Asp Gly Lys Ser Thr Arg Tyr Trp Asp Cys
1               5                   10                  15

Cys Lys Pro Ser Cys
            20

<210> SEQ ID NO 10
<211> LENGTH: 16
<212> TYPE: PRT
<213> ORGANISM: Humicola insolens

<400> SEQUENCE: 10

Gln Gln Ala Gly Ser Ala Asp Gly Lys Ser Thr Arg Tyr Trp Asp Cys
1               5                   10                  15

<210> SEQ ID NO 11
<211> LENGTH: 6
<212> TYPE: PRT
<213> ORGANISM: Humicola insolens

<400> SEQUENCE: 11

Tyr Gly Gly Ile Ser Ser
1               5

<210> SEQ ID NO 12
<211> LENGTH: 6
<212> TYPE: PRT
<213> ORGANISM: Humicola insolens

<400> SEQUENCE: 12

Phe Pro Asp Ala Leu Lys
1               5

<210> SEQ ID NO 13
<211> LENGTH: 15
<212> TYPE: PRT
<213> ORGANISM: Humicola insolens

<400> SEQUENCE: 13

Phe Asp Trp Phe Lys Asn Ala Asp Asn Pro Ser Phe Ser Phe Arg
1               5                   10                  15

<210> SEQ ID NO 14
<211> LENGTH: 22
<212> TYPE: DNA
<213> ORGANISM: Humicola insolens
<220> FEATURE:
<221> NAME/KEY: misc_feature
<222> LOCATION: (3)..(3)
<223> OTHER INFORMATION: inosine
<221> NAME/KEY: misc_feature
<222> LOCATION: (10)..(10)
<223> OTHER INFORMATION: Inosine

<400> SEQUENCE: 14
gcngactggn aaagtcagct ac                                          22

<210> SEQ ID NO 15
<211> LENGTH: 20
<212> TYPE: DNA
<213> ORGANISM: Humicola insolens
```

```
<220> FEATURE:
<221> NAME/KEY: misc_feature
<222> LOCATION: (3)..(3)
<223> OTHER INFORMATION: Inosine
<221> NAME/KEY: misc_feature
<222> LOCATION: (10)..(10)
<223> OTHER INFORMATION: Inosine

<400> SEQUENCE: 15
gcngactggn aaagagctac                                                  20

<210> SEQ ID NO 16
<211> LENGTH: 23
<212> TYPE: DNA
<213> ORGANISM: Humicola insolens
<220> FEATURE:
<221> NAME/KEY: misc_feature
<222> LOCATION: (2)..(2)
<223> OTHER INFORMATION: Insoine

<400> SEQUENCE: 16
cngcagttct ttagaaccaa gtc                                              23

<210> SEQ ID NO 17
<211> LENGTH: 23
<212> TYPE: DNA
<213> ORGANISM: Humicola insolens

<400> SEQUENCE: 17
gtgatgaggg ctggcgacag gcc                                              23

<210> SEQ ID NO 18
<211> LENGTH: 23
<212> TYPE: DNA
<213> ORGANISM: Humicola insolens

<400> SEQUENCE: 18
ctgccacctc tattgccggc agc                                              23

<210> SEQ ID NO 19
<211> LENGTH: 23
<212> TYPE: DNA
<213> ORGANISM: Humicola insolens

<400> SEQUENCE: 19
cccgacgccc tcaagcccgg ctg                                              23

<210> SEQ ID NO 20
<211> LENGTH: 23
<212> TYPE: DNA
<213> ORGANISM: Humicola insolens

<400> SEQUENCE: 20
ggctggagcg gctgcaccac ctg                                              23

<210> SEQ ID NO 21
<211> LENGTH: 23
<212> TYPE: DNA
<213> ORGANISM: Humicola insolens

<400> SEQUENCE: 21
gacctgacgg aagctgaagc tcg                                              23

<210> SEQ ID NO 22
<211> LENGTH: 23
```

-continued

```
<212> TYPE: DNA
<213> ORGANISM: Humicola insolens

<400> SEQUENCE: 22
agcagtgcag ccgctgggag tcg                                          23

<210> SEQ ID NO 23
<211> LENGTH: 23
<212> TYPE: DNA
<213> ORGANISM: Humicola insolens

<400> SEQUENCE: 23
tggcagatga ggacgtggtg ttg                                          23

<210> SEQ ID NO 24
<211> LENGTH: 23
<212> TYPE: DNA
<213> ORGANISM: Humicola insolens

<400> SEQUENCE: 24
cgcagccgga cttggcgtcg aag                                          23

<210> SEQ ID NO 25
<211> LENGTH: 30
<212> TYPE: DNA
<213> ORGANISM: Humicola insolens

<400> SEQUENCE: 25
atgcgttcct ccctctcct ccgctccgcc                                    30

<210> SEQ ID NO 26
<211> LENGTH: 30
<212> TYPE: DNA
<213> ORGANISM: Humicola insolens

<400> SEQUENCE: 26
tacaggcact gatggtacca gtcattaatc                                   30

<210> SEQ ID NO 27
<211> LENGTH: 36
<212> TYPE: DNA
<213> ORGANISM: Humicola insolens

<400> SEQUENCE: 27
gagcgccaga actgtggatc cacttggtga gcaatg                            36

<210> SEQ ID NO 28
<211> LENGTH: 35
<212> TYPE: DNA
<213> ORGANISM: Humicola insolens

<400> SEQUENCE: 28
tccgccgttc tgagcggatc caggcgtttg gcgcg                             35

<210> SEQ ID NO 29
<211> LENGTH: 36
<212> TYPE: DNA
<213> ORGANISM: Humicola insolens

<400> SEQUENCE: 29 gccgccagc aggcgggatc cctcaccacc gagagg                             36

<210> SEQ ID NO 30
```

```
<211> LENGTH: 36
<212> TYPE: DNA
<213> ORGANISM: Humicola insolens

<400> SEQUENCE: 30
tgatcgtcga gtcagggatc cagaatttac aggcac                              36

<210> SEQ ID NO 31
<211> LENGTH: 30
<212> TYPE: DNA
<213> ORGANISM: Humicola insolens

<400> SEQUENCE: 31
ccggtgttgg ccggatccgc tgatggcaag                                     30

<210> SEQ ID NO 32
<211> LENGTH: 30
<212> TYPE: DNA
<213> ORGANISM: Humicola insolens

<400> SEQUENCE: 32
taaggccctc aaggatccct gcgtctacag                                     30

<210> SEQ ID NO 33
<211> LENGTH: 32
<212> TYPE: DNA
<213> ORGANISM: Humicola insolens

<400> SEQUENCE: 33
gtcatgaagc ttcattaagg tacgtatgca ac                                  32

<210> SEQ ID NO 34
<211> LENGTH: 32
<212> TYPE: DNA
<213> ORGANISM: Humicola insolens

<400> SEQUENCE: 34
ggtgatggat ccggcctgct gggcagcgac gc                                  32
```

SYSTEMS FOR THE MASS PRODUCTION OF PROTEINS OR PEPTIDES BY MICROORGANISMS OF THE GENUS HUMICOLA

BACKGROUND OF THE INVENTION

1. Field of the Invention

The present invention relates to a system for a large amount of expression or secretion of a protein or peptide in Humicola microorganisms, in particular, *Humicola insolens*.

2. Description of the Related Art

Mold fungi is known to secrete proteins extracellularly. Thus, has been studied for developing highly productive mutant cells and processes for efficient production of proteins.

A typical example of such studies is to artificially create mutants by exposure to ultraviolet rays or by the use of a mutagen, and to select a strain which produces the target protein in a large volume.

However, these techniques may not be suitable for expressing an enzyme whose activity relies on the coordination of several different proteins, or for improving the characteristics of such an enzyme. Furthermore, when producing a protein which imparts a lethal or adverse effect on the growth of a host cell, the productivity of the target protein is generally difficult to increase by a mutation.

On the other hand, the recent progress in the study of genetic recombination for producing a target protein have enabled a large amount of production for heterogenous proteins, as well as proteins endogenous to the host cells but expressed only in small amounts. Successful production ranging from about 1.0 to 3.3 g per one liter of culture has been reported in some mold fungi, such as *Aspergillus nidulans* (G. L. Gray, et al., Gene, 48,41, 1986), *Aspergillus oryzae* (T. Christensen, et al., Bio/Technology, 6, 1419, 1988), *Trichoderma reesei* (Taina Karhunen, et al., Mol. Gen. Genet. 241, 515–522, 1993), and *Trichoderma viride* (C. Cheng, et al., Agric. Biol. Chem., 55, 1817, 1991).

*Humicola insolens* is another example of a halophilic mold fungus having remarkable capability of protein secretion. This species is also known to produce various types of cellulase of industrial utility (WO91/17243 (Japanese Patent Laid-Open No. 5-509223)).

However, the useful content of the protein secretion from *Humicola insolens* accounts only for a few percent. If a process which enables fungus to express and secrete these small proportions of useful components in a large quantity is established, the benefit of the final products can be dramatically improved. Furthermore, a process that would enable a large quantity of expression of heterogenous genes in *Humicola insolens* may allow various enzymes and useful proteins to be produced in a single-step procedure, helping lower the cost of production. In addition, since *Humicola insolens* is a halophilic mold fungus with an optimum incubation temperature of about 37° C., it is hardly contaminated by other germs during incubation, making it further advantageous as a host for producing useful proteins.

Furthermore, systems for transforming *Humicola insolens* have been established, as has been disclosed by some of the inventors in Japanese Patent Laid-Open No. 8-56663, allowing the fungus to be used for genetic recombination.

Still, it has been awaited to develop an effective expression vector system which allows *Humicola insolens* to express and secrete a target protein at a high yield.

SUMMARY OF THE INVENTION

The inventors have now established a process for producing a target protein in a large quantity in Humicola, in particular, *Humicola insolens*.

Thus, the object of the present invention is to a provide expressing systems enabling production of a protein in a large amount in Humicola, in particular, *Humicola insolens*, and particularly host-vector systems and a process for producing a protein using the host-vector systems.

Moreover, according to the preferred embodiment of the present invention, there is provided a highly efficient system for producing a protein, in which the productivity of the target protein is as high as about 4.5 g per one liter of culture, or 10 to 16 times that in the original strain.

DESCRIPTION OF THE PREFERRED EMBODIMENTS

Deposit of Microorganisms

Figure 1:
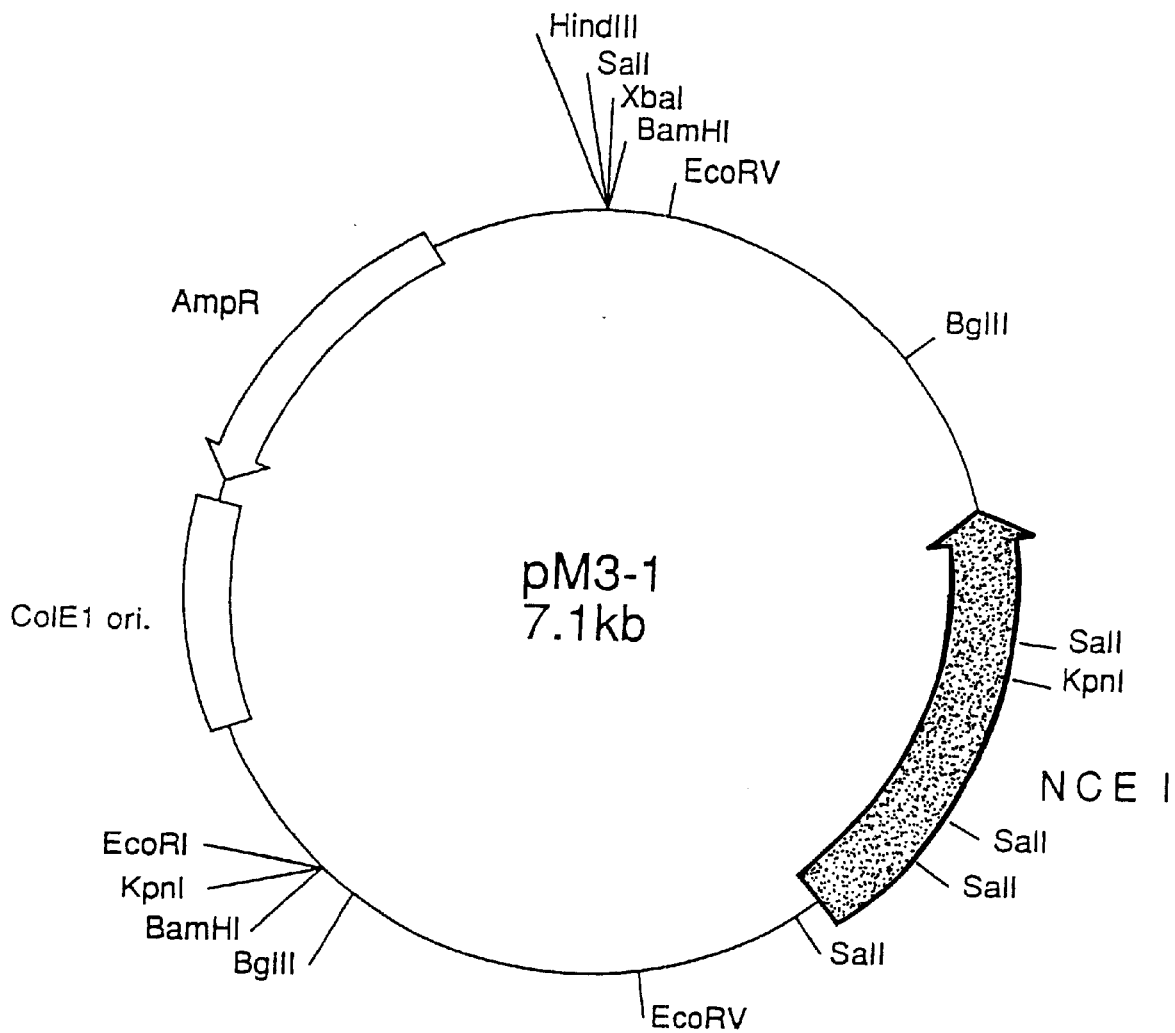
FIG. 1 is the restriction map of plasmid pM3-1.

The *E. coli* JM109 strain transformed by plasmid pM3-1, which is represented by the map shown in FIG. 1, has been deposited in the National Institute of Bioscience and Human-Technology, Ministry of International Trade and Industry of Japan (Higashi 1-1-3, Tsukuba-shi, Ibaraki-ken, Japan), under Accession No. FERM BP-5971 (originally under Accession No. FERM P-14459 as of Aug. 3, 1994).

Figure 2:
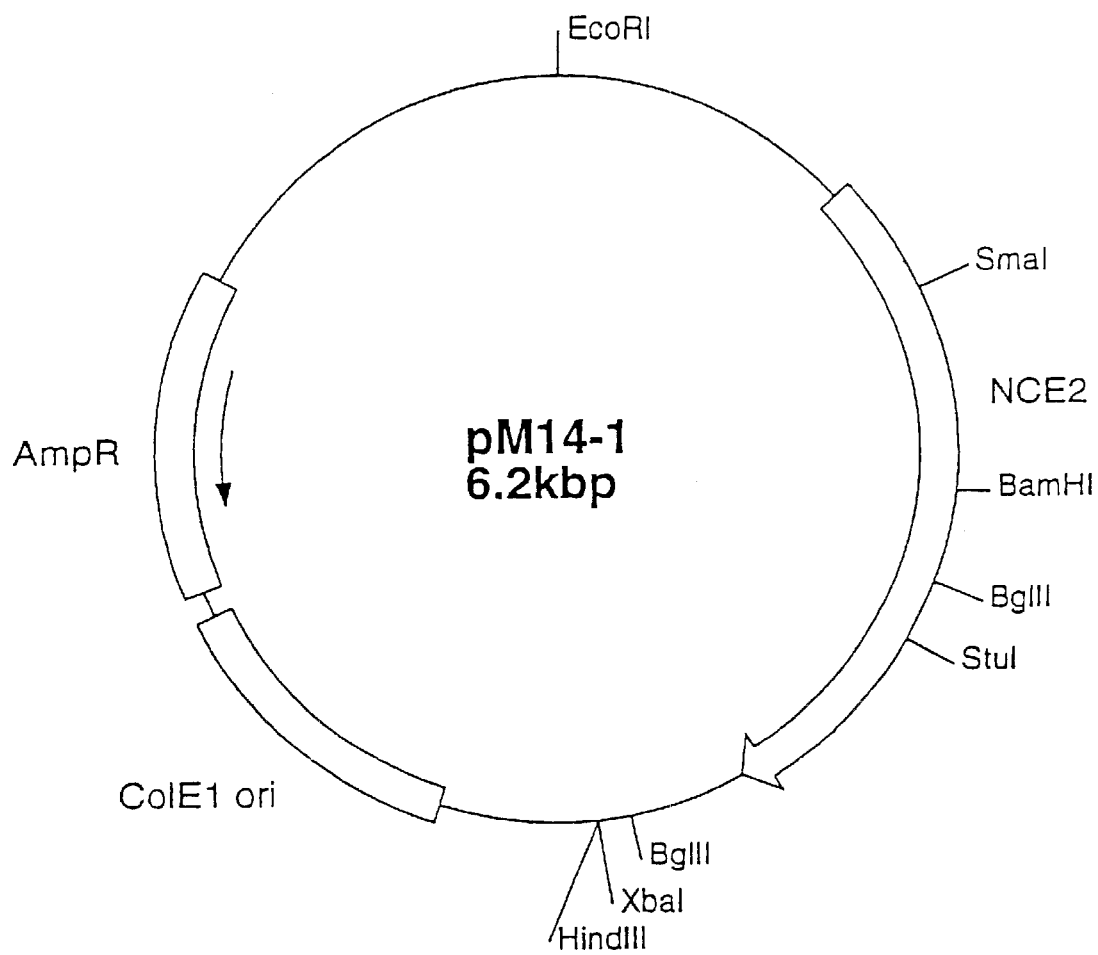
FIG. 2 is the restriction map of plasmid pM14-1.
Figure 3:
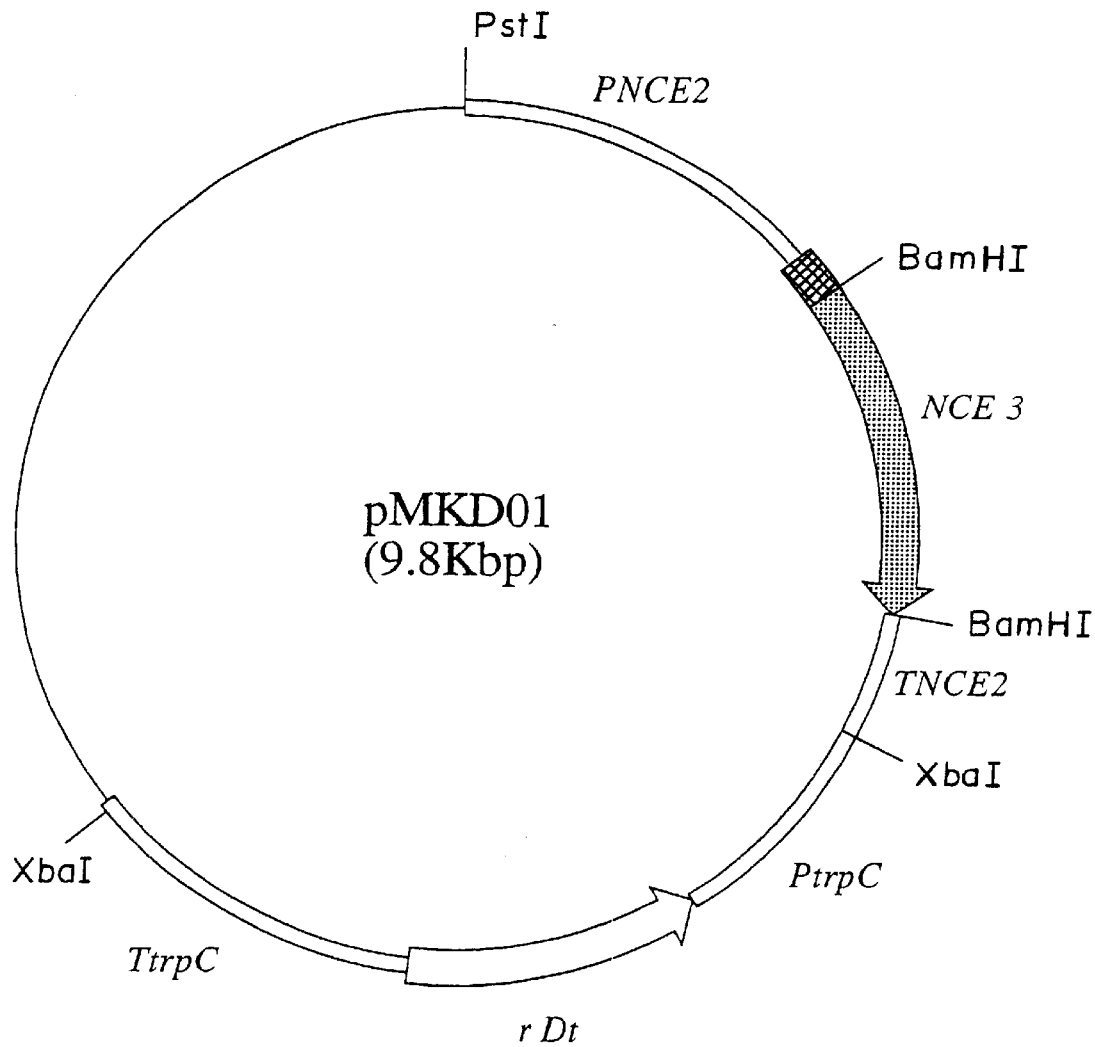
FIG. 3 is the restriction map of plasmid vector pMKD01.
Figure 4:
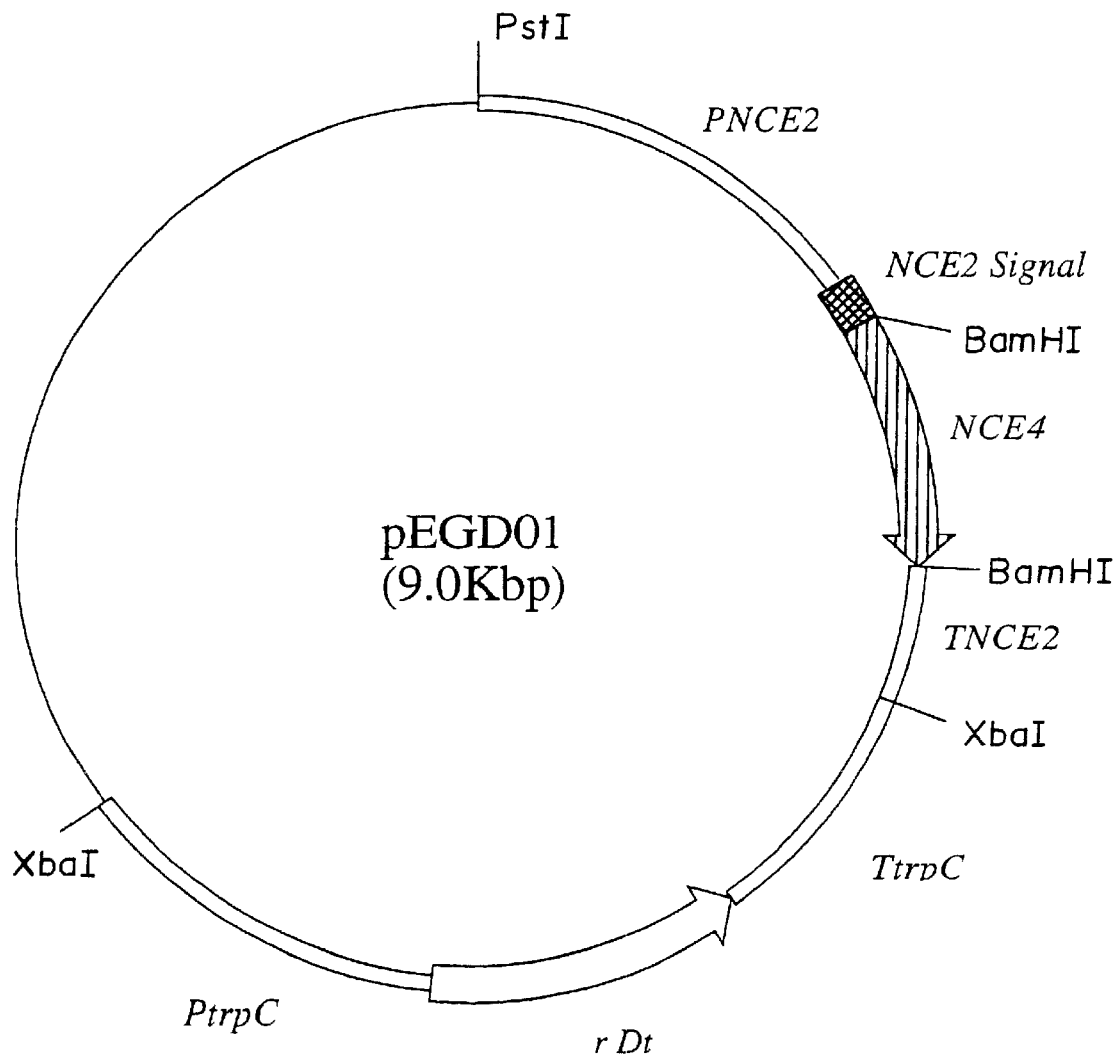
FIG. 4 is the restriction map of plasmid vector pEGD01.
Figure 5:
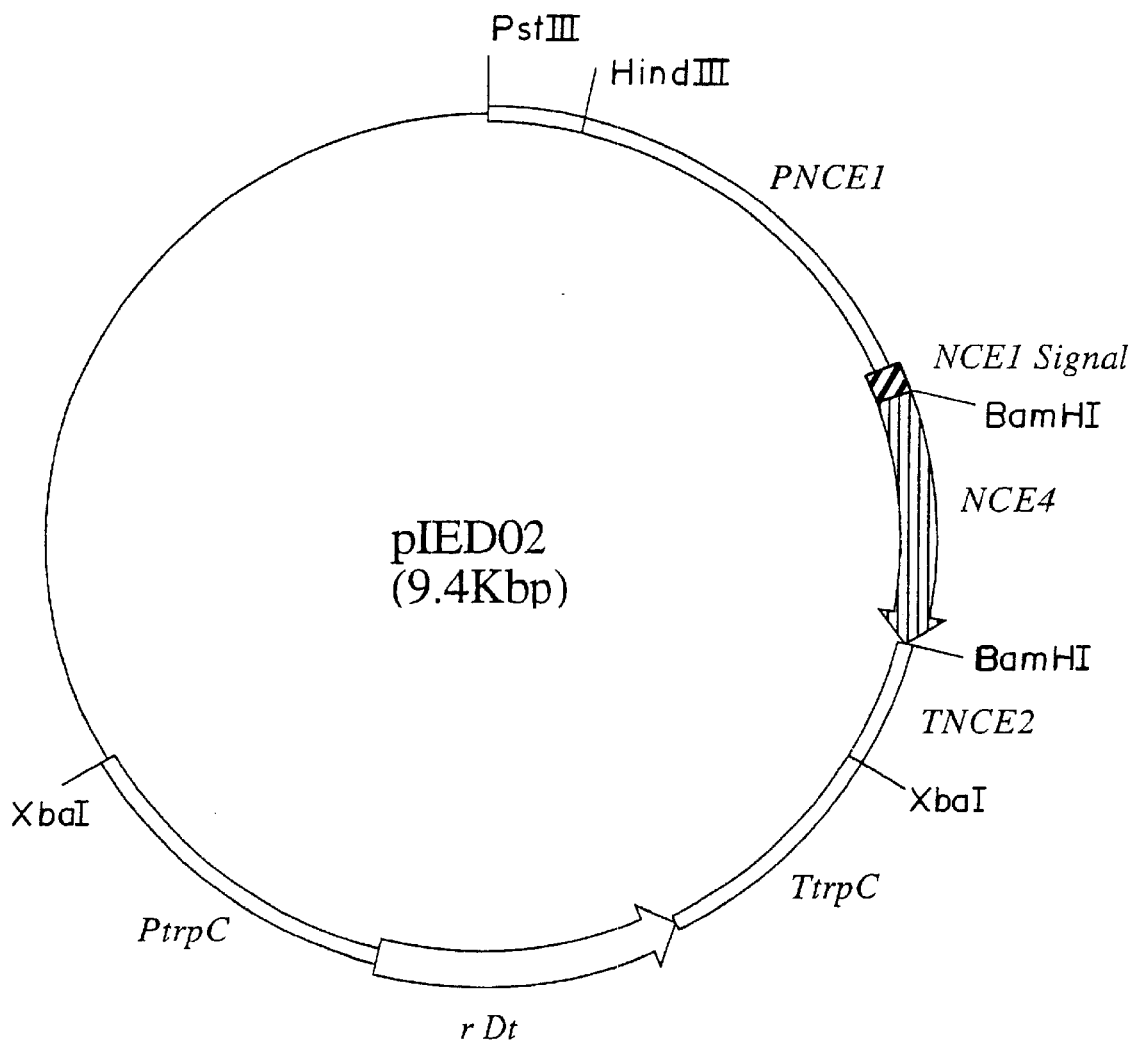
FIG. 5 is the restriction map of plasmid vector pIED02.

The *E. coli* JM109 strain transformed by plasmid pM14-1, which is represented by the map shown in FIG. 2, has been deposited in the National Institute of Bioscience and Human-Technology, Ministry of International Trade and Industry of Japan, under Accession No. FERM BP-5972 (originally under Accession No. FERM P-14585 as of Oct. 18, 1994).

The *E. coli* JM109 strain transformed by expression vector pMKD01 according to the present invention has been deposited in the National Institute of Bioscience and Human-Technology, Ministry of International Trade and Industry of Japan, under Accession No. FERM BP-5974 (originally under Accession No. FERM P-15730 as of Jul. 12, 1996).

The *E. coli* JM109 strain transformed by expression vector pEGD01 according to the present invention has been deposited in the National Institute of Bioscience and Human-Technology, Ministry of International Trade and Industry of Japan, under Accession No. FERM BP-5973 (originally under Accession No. FERM P-15729 as of Jul. 12, 1996).

The *E. coli* JM109 strain transformed by expression vector pIED02 according to the present invention has been deposited in the National Institute of Bioscience and Human-Technology, Ministry of International Trade and Industry of Japan, under Accession No. FERM BP-5975 (originally under Accession No. FERM P-15731 as of Jul. 12, 1996).

The *E. coli* JM109 strain transformed by expression vector pNCE4Sal according to the present invention has been deposited in the National Institute of Bioscience and Human-Technology, Ministry of International Trade and Industry of Japan, under Accession No. FERM BP-5976 (originally under Accession No. FERM P-15732 as of Jul. 12, 1996).

The *Humicola insolens* MN200-1 strain, which may be used as a host to the expression vectors according to the present invention, has been deposited in the National Institute of Bioscience and Human-Technology, Ministry of International Trade and Industry of Japan, under Accession No. FERM BP-5977 (originally under Accession No. FERM P-15736 as of Jul. 15, 1996).

Definitions

The terms "protein" and "peptide" are herein used synonymously unless otherwise noted. Furthermore, the term "modified sequence" as used herein is intended to mean a nucleotide sequence or an amino acid sequence comprising an insertion, substitution or deletion of one or more nucleotides or amino acids therein, or an addition to either or both of the terminals thereof.

Deposit Information

A deposit for expression vectors and plasmids discussed in the following specification below has been made at the:
National Institute of Bioscience and Human-Technology
Agency of Industrial Science & Technology
Ministry of International Trade and Industry of Japan.
Higashi 1-1-3, Tsukuba-shi, Ibaraki-ken, Japan The deposit number and the date of the deposit are as follows:

1) Expression vector pMKD01
   Deposit number: FERM BP-5974
   The date of the deposit: Jul. 12, 1996
2) Expression vector pEGD01
   Deposit number: FERM BP-5973
   The date of the deposit: Jul. 12, 1996
3) Expression vector pIED02
   Deposit number: FERM BP-5975
   The date of the deposit: Jul. 12, 1996
4) Plasmid pM3-1
   Deposit number: FERM BP-5971
   The date of the deposit: Aug. 3, 1994
5) Plasmid pM14-1
   Deposit number: FERM BP-5972
   The date of the deposit: Oct. 18, 1994.

Regulator Sequence of *Humicola insolens*

In the expressing systems in Humicola according to the present invention, a regulator sequence derived from *Humicola insolens* is to be used. In the present invention, the term "regulator sequence" is intended to mean at least one selected from the group consisting of a promoter, a signal sequence, and a terminator.

The regulator sequence according to the present invention is preferably the regulator sequence of the cellulase NCE1 gene derived from *Humicola insolens* as disclosed in Japanese Patent Laid-Open No. 8-56663, or the regulator sequence of the cellulase NCE2 gene derived from *Humicola insolens* as disclosed in Japanese Patent Laid-Open No. 8-126492. More specifically, these regulatory sequences are those of NCE1 in plasmid pM3-1 and NCE2 in plasmid pM14-1 in the strains deposited under Accession Nos. FERM BP-5971 and FERM BP-5972, respectively.

Examples of the preferable promoter sequences according to the present invention include the sequences found in the region of about 1500 bp on the upstream side of the N-terminal of the NCE1 gene on plasmid pM3-1, which is represented by the map shown in FIG. 1, such as the sequence from the N-terminal of the NCE1 gene up to the Bgl II site as shown in the Figure.

Other examples of the preferable promoter sequences according to the present invention include the sequences found in the region of about 1500 bp on the upstream side of the N-terminal of the NCE2 gene on plasmid pM14-1, which is represented by the map shown in FIG. 2, such as the sequence from the N-terminal of the NCE2 gene up to the EcoR I site as shown in the Figure.

It should be noted that, the promoter sequences according to the present invention are not limited to the entire sequences of the above regions, but include their modified sequences having high promoter activity. In the present invention, the term "high promoter activity" is intended to mean a high promoter activity which effectively expresses the NCE4 gene, which is described later. More specifically, the term refers to a promoter activity which expresses 2.0 g of NCE4, preferably 4.0 g, and more preferably 4.5 g, per one liter of medium. It is obvious that those skilled in the art would easily be able to presume and produce such modified sequences, if they were provided with the findings described later in the Examples, the strains deposited under Accession No. FERM BP-5971 and FERM BP-5972, and the maps shown in FIGS. 1 and 2.

Examples of the preferable signal sequences according to the present invention include the signal sequences of cellulases NCE1 and NCE2. More specifically, these sequences are the nucleotide sequence encoding the sequence of −22 to −1 in the amino acid sequence of SEQ ID No. 1, and the nucleotide sequence encoding the sequence of −23 to −1 in the amino acid sequence of SEQ ID No. 2. The present invention also includes nucleotide sequences encoding modified sequences of the above amino acid sequences which retain signal sequence activity. It is obvious for such modified sequences that those skilled in the art would easily be able to presume and produce such modified sequences, if they were provided the findings described later in the examples, the bacterial strains deposited under Accession No. FERM BP-5971 and FERM BP-5972, and the maps shown in FIGS. 1 and 2.

In the practical application of these sequences, it is also obvious for those skilled in the art that one or more amino acids on the N-terminal of NCE1 or NCE2 may be added, in addition to the above signal sequences. Therefore, in the application of these signal sequences, the target protein may be a fused protein which comprises a peptide consisting of one or more amino acids on the N-terminal of NCE1 or NCE2, or a fused protein comprising NCE1 or NCE2.

Examples of the preferable terminator sequences according to the present invention include the sequences found in the region of about 1400 bp on the downstream side of the C-terminal of the NCE1 gene on plasmid pM3-1, which is represented by the map shown in FIG. 1, such as the sequence from the C-terminal of the NCE1 gene down to the Bgl II site.

Other examples of the preferable terminator sequences according to the present invention include the sequences found in the region of about 500 bp on the downstream side of the C-terminal of the NCE2 gene on plasmid pM14-1, which is represented by the map shown in FIG. 2, such as the sequence from the C-terminal of the NCE2 gene down to the Bgl II site.

It should be noted that, the terminator sequences according to the present invention are not limited to the entire sequences of the above regions, but include their modified sequences retaining terminator activity.

These regulator sequences, particularly the promoter sequences of NCE1 and NCE2, enable highly efficient expression the NCE4 gene. Thus, according to a preferred embodiment of the present invention, there is provided a regulator sequence used preferably in the expression of the NCE4 gene and, in particular, a promoter sequence used preferably in the expression of the NCE4 gene. According to a preferred embodiment of the present invention, the productivity of cellulase NCE4 is as high as 2.0 g, preferably 4.0 g, and more preferably about 4.5 g, per one liter of culture, or 10 to 16 times that in the original strain from which the enzyme is derived.

Expression Vector and Host

According to the present invention, there is provided expression vectors for expressing a target protein using the above regulator sequences.

The expression vector according to the first embodiment of present invention comprises the above regulator sequence and, as necessary, a gene marker. The expression vector according to the present invention further comprises, in addition to the expression vector according to the first embodiment, a nucleotide sequence encoding a target protein which is operatively linked with the regulator sequence of the expression vector. Thus, the scope of the present invention embraces expression vectors comprising at least one selected from the group consisting of the promoter, the signal sequence, and the terminator according to the present invention described above.

Since the promoter sequence according to the present invention is of extremely high utility as described above, according to a preferred embodiment of the present invention, there is provided an expression vector which at least comprises the promoter sequence according to the present invention. The signal sequence and the terminator sequence of the expression vectors are preferably the signal sequence and the terminator sequence according to the present invention described above, although other sequences may still be used. Specific examples of such vectors include transformants of expression vectors pMKD01, pEGD01 and pIED02 as constructed later in the Examples, from which the NCE3 and NCE4 genes are removed.

The expression vectors according to the present invention are preferably constructed from vectors which are replicable in the host cell, such as plasmids. Examples of such vectors include pUC vector, pTV vector, pBluescript, and pBR322, which are all replicable in *E. coli*. The vectors according to the present invention may be constructed by the standard techniques for genetic recombination.

The gene marker may be selected as appropriate, depending on the method for selecting the transformant, such as from genes encoding drug resistance or genes complementing for auxotrophy. The drug resistant gene for use in the present invention is not limited in any way, provided that the host cell is sensitive to that drug. For example, when *Humicola insolens* is used as a host, the destmycin resistant gene derived from Streptomyces rimofaciens, hygromycin B resistant gene derived from *E. coli*, bleomycin resistant gene derived from Streptococcus hindustanus, or bialophos resistant gene derived from *Streptomyces hygroscopicus* is preferably be used.

In the preferred embodiment of the present invention, the promoter and terminator of the *Aspergillus nidulans* trp C gene which are obtained using known techniques (Mullaney, E. J. et al., Mol. Gen. Genet. 199: 37–45, 1985) are preferably used in the form of a cassette which can express destmycin resistant gene (Japanese Patent Laid-Open No. 59-175889). The expression vectors according to the present invention can be used for the expression and production of a variety of target proteins and peptides. In the present invention, the term "target protein or peptide" is intended to mean proteins expressed by *Humicola insolens* only in a small amount, in addition to proteins heterogenous to the species, i.e., proteins which do not intrinsically exist in *Humicola insolens*. Examples of genes encoding a target protein which reside on the expression vector according to the present invention include genes encoding cellulase, amylase, lipase, protease, phytase, and other industrially useful proteins, as well as the transformants of these genes comprising artificial improvements.

The expression vector according to the present invention constitutes an expressing system when combined with a host Humicola. The Humicola microorganism for use in the preferred embodiment of the present invention is *Humicola insolens*.

NCE4 Gene

According to a preferred embodiment of the present invention, the expressing systems according to the present invention can be preferably used to produce cellulase NCE4 derived from *Humicola insolens*, or its modified proteins, as a target protein. The term "cellulose NCE4 derived from *Humicola insolens*" as used herein is intended to mean the protein of SEQ ID No. 3. This protein is a cellulase enzyme which has now been isolated by a group including the inventors, as described later in the Examples. Furthermore, the term "modified protein" as used herein is intended to mean a protein whose amino acid sequence comprises a modification such as an addition, insertion, removal, deletion or substitution of one or more amino acids in the amino acid sequence of the above protein, and which retains cellulase activity comparable to that of cellulase NCE4, particularly endoglucanase activity.

According to a preferred embodiment of the present invention, examples of preferable vectors for use in the above systems for expressing cellulase NCE4 include expression vectors pMKD01, pEGD01 and pIED02, which are constructed as described later in the Examples.

Using the expression vector according to the present invention, the host cell can be transformed by the standard techniques for genetic recombination, such as by the process disclosed in Japanese Patent Laid-Open No. 8-56663, or by electropolation.

Production of Target Protein

According to the present invention, the target protein can be produced by incubating a host cell, which have been transformed by the expression vector according to the present invention, in a suitable medium, and recovering the target protein or peptide from the culture.

According to the preferred embodiment of the present invention, there is provided a highly efficient system for producing a target protein, in which the productivity of the target protein is as high as 2.0 g, preferably 4.0 g, and more preferably about 4.5 g, per one liter of culture, or 10 to 16 times that in the original strain. For example, when *Humicola insolens* is used as a host cell, 2.0 g, preferably 4.0 g, and more preferably at least 4.5 g of target protein can be produced per one liter of culture. These figures are significantly higher than in previously known systems for expressing proteins, indicating that the systems for expressing a target protein according to the present invention are of extremely high utility.

For example, the systems for producing target proteins according to the present invention allow a large amount of production of cellulase NCE3 or NCE4. Given that these enzymes intrinsically have high activity, the systems for producing proteins according to the present invention enable the efficient production of cellulase preparations, which are useful for nap removal or weight reduction in cellulose-containing textiles, or decoloration of these textiles which have been denim-stained.

In the process for producing a target protein according to the present invention, the transformant can be incubated in a liquid medium of the standard composition containing a carbon source, a nitrogen source, inorganic salts, a growth factor, and other components, using a procedure such as incubation under aerobic conditions, incubation under shaking, incubation with electrical agitation, or incubation in depth. An example of the pH range for the medium is about 7 to 8. When *Humicola insolens* is used as host cells, incubation of the transformant can be performed under the standard conditions applicable to the incubation of the original *Humicola insolens*, e.g., 15 to 45° C., preferably 35 to 40° C., for a period of about 24 to 240 hours.

The protein or peptide obtained according to the present invention can be recovered from the culture using the standard techniques for separation, depending on the characteristics of the protein or peptide, such as extraction with a solvent, the use of an ion exchange resin, absorption or distribution column chromatography, gel filtration, dialysis, or precipitation. These techniques may be used either individually or in combination as appropriate.

EXAMPLES

The present invention is further illustrated by the following Examples, which are not intended as a limitation of the invention.

Example A1

Isolation and Purification of a Component having Tencel Nap Removing Activity from *Humicola insolens*

*Humicola insolens* MN200-1 was incubated at 37° C. in medium (N) (5.0% avisel, 2.0% yeast extract, 0.1% polypepton, 0.03% calcium chloride and 0.03% magnesium sulfate, pH 6.8). After 7 days of incubation, the culture was centrifuged at 7000 rpm for 20 minutes for removing the cell bodies to give a crude cellulase solution.

The cellulase solution was eluted and separated by hydrophobic chromatography (Phenyl-Sepharose High Performance 16/100, Pharmacia Biotech), using 50 mM phosphate buffer (pH 7.0) at an ammonium sulfate gradient of 1 to 0 M. The fraction which eluted at a gradient of 0.1 to 0 M exhibited a high tencel nap removing activity. This fraction was again eluted and separated by hydrophobic chromatography (Phenyl-Sepharose High Performance 16/100), using 50 mM phosphate buffer (pH 7.0) at an ammonium sulfate gradient of 0.4 to 0 M.

The fraction thus obtained was eluted and separated by reversed-phase partition chromatography (Source 15 ISO, Pharmacia Biotech), using 50 mM phosphate buffer (pH 7.0) at an ammonium sulfate gradient of 1 to 0 M. The fraction which eluted at a gradient of 0 M exhibited a high tencel nap removing activity. This fraction was again eluted by reversed-phase partition chromatography (Source 15 PHE, Pharmacia Biotech), using 50 mM phosphate buffer (pH 7.0) at an ammonium sulfate gradient of 1 to 0 M, to give a fraction with high tencel nap removing activity as purified enzyme NCE4. The fraction appeared as a single band with a molecular weight of 43 kDa on SDS-PAGE.

Example A2

Partial Amino Acid Sequence of Cellulase NCE4

(1) Amino acid sequencing on N-terminal

In order to sequence the amino acids on the N-terminal of the protein purified in Example 1, the sample was separated by column chromatography using an FPLC system (Pharmacia Biotech; column: RESOURCE (TM) RPC 3 ml; gradient: 5 to 60% acetonitrile containing 0.1% TFA).

The major peaks were separated and freeze-dried, then dissolved in a small amount of water. The solution was electrophoresed using 8% Gel SDS-PAGE mini (Difco). The proteins were electrically transferred onto a PVDF membrane (Millipore), using a MultiPhore II electrophoretic analyzer (Pharmacia Biotech). The proteins were stained with Comazy Brilliant Blue R-250 (Nakalytesk), then decolored, washed in water, and dried in air. The region blotted with a protein having a molecular weight of 43 kDa was cut out, and analyzed by protein sequencer Model 492 (Perkin Elmer) to determine the 15-mer amino acid sequence on the N-terminal. The determined amino acid sequence was as follows:

Amino acid sequence on N-terminal: Ala-Asp-Gly-Lys-Ser-Thr-Arg-Tyr-Trp-Asp-(Cys)-(Cys)-Lys-Pro-Ser (15 amino acids; amino acids 6–20 of SEQ ID NO. 6)

(2) Peptide Mapping

The protein purified using FPLC in (1) above was freeze-dried, and dissolved in 100 mM ammonium bicarbonate buffer (pH 8.0). After about 1 mol of trypsin (Promega) per 20 mol of protein was added, the solution was allowed to react at 37° C. for 48 hours. The resultant protein fragments were separated by column chromatography using the Model 172$\mu$ preparative HPLC system (Perkin Elmer; column:C8, 220 x 2.1 mm; gradient: 0.1% TFA, 0% acetonitrile to 0.085% TFA, 35% acetonitrile) to obtain three types of peptides. The peptides were sequenced by using the same protein sequencer as above. The determined amino acid sequences were as follows:

TP-1: Tyr-Gly-Gly-Ile-Ser-Ser SEQ ID NO. 8 (6 amino acids) TP-2: Phe-Pro-Asp-Ala-Leu-Lys SEQ ID NO. 9 (6 amino acids) TP-3: Phe-Asp-Trp-Phe-Lys-Asn-Ala-Asp-Asn-Pro-Ser-Phe-Ser-Phe-Arg SEQ ID NO. 10.

The amino acid sequence on the N-terminal and the amino acid sequences determined by peptide mapping were homologous to the amino acid sequence of the 43 kDa endoglucanase obtained from the *Humicola insolens* DSM 1800 strain, which is disclosed in Patent Publication WO91/17243 (Japanese Patent Laid-Open No. 5-509223). This fact strongly suggests that the above protein was a type of cellulase.

The sequence of the above protein was compared with the sequence registered in Protein Identification Resource (PIR) R44.0, March 1995, or SWISS-PROT R31.0, March 1995. The result revealed that there is no sequence, that was identical, although there are some having partially homologous, showing that the above protein was novel.

Example A3

Preparation of a Genome DNA Library

The genome DNA was isolated according to the procedure described by Horiuchi, et al. (Hiroyuki Horiuchi, et al., J. Bacteriol., 170: 272–278, 1988) as follows:

The *Humicola insolens* MN200-1 was incubated at 37° C. in medium (N) described above. After 2 days of incubation, cells were recovered by centrifugation at 3500 rpm for 10 minutes. The cells were treated with phenol, proteinase K, and ribonuclease A, followed by polyethylene glycol (PEG) precipitation, to obtain the genome DNA.

Then, the *Humicola insolens* genome DNA was digested with Sau3A I. The result of agarose gel electrophoresis showed that the DNA was decomposed to 9 to 23 kbp fragments. The DNA fragments were recovered by ethanol precipitation, and ligated with the BamH I arm of the phage vector EMBL3 cloning kit (Stratagene), using T4 ligase (Toyobo). After ethanol precipitation, the ligated fragments were dissolved in TE buffer (10 mM Tris-HCl (pH 8.0), and 1 mM EDTA).

The entire mixture of the ligated DNA fragments was packaged to a lambda head according to the procedure described by Hohn, B. (Hohn, B. Methods Enzymol., 68: 299–309, 1979), using the frozen package components and the Gigapack II packaging kit (Stratagene). The resultant phage was used to infect the E. coli LE392 strain to obtain a phage library of 5×10$^4$, which was then used for cloning the target gene.

Example A4

Preparation of a Long-Strand Probe by PCR

Using the entire DNA of Humicola insolens as a template, a long DNA probe was prepared by PCR amplification.

For use as primers, DNA fragments having nucleotide sequences encoding the amino acid sequence on the N-terminal and the amino acid sequence denoted by '*' in peptide TP-3 were produced. The sequences of the synthetic oligonucleotides used as primers were as follows:
NCE4N1: 5'-GCXGA(CT)GGXAA(AG)TC(AGCT)AC-3'SEQ ID NO. 11 (17-mer)
NCE4N2: 5'-GCXGA(CT)GGXAA(AG)AG(CT)AC-3'SEQ ID NO. 12 (17-mer)
NCE4C: 5'-CXGC(AG)TT(CT)TT(AG)AACCA(AG)TC-3'SEQ ID NO. 13 (19-mer)
(X: inosine)
The procedure for PCR was as follows:
First, 1 µM each of NCE4N1 and NCE4C, or 1 µM each of NCE4N2 and NCE4C were added as primers per 1 µg of Humicola insolens genome DNA, to prepare two types of tubes. They were denatured by heating at 95° C. for 5 minutes in the presence of dNTP, and mixed with Taq polymerase (recombinant Taq, Takara Shuzo). Then, the DNA was amplified through 25 cycles of reactions at 94° C. for 1 minute, at 45° C. for 2 minutes, and at 72° C. for 3 minutes. As a result, about 750 bp DNA fragment was amplified in one of the two samples in which NCE4N1 and NCE4C were used as primers. The DNA fragment was used as a screening probe in the subsequent experiments.

Example A5

Gene Cloning of Cellulase Component NCE4

(1) Screening by plaque hybridization

The DNA fragment (100 ng) of about 750 bp, which has been by amplified by PCR, was labeled by using an ECL direct DNA/RNA labeling detection system (Amersham).

Phage plaque was prepared according to the procedure described in Example A3, and transferred onto a Hybond-N+ nylon transfer membrane (Amersham). Then, the DNA was denatured with 0.4 N sodium peroxide, washed in SSC (15 mM trisodium citrate and 150 mM sodium chloride) at 5-fold concentration, then dried to fix. After prehybridization at 42° C. for 1 hour according to the instruction of the kit, the labeled probe was added. Then, the DNA was hybridized for at 42° C. for 4 hours. The label was washed according to the instruction of the kit, i.e., washed twice in SSC at 0.5-fold concentration containing 0.4% SDS and 6 M urea at 42° C. for 20 minutes, and then twice in SSC at 2-fold concentration at room temperature for 5 minutes.

After the probe was washed, the nylon membrane was immersed in the supplied detection solution for 1 minute, then used to expose a hyperfilm ECL (Amersham). Four clones turned out positive.

(2) Preparation of Phage DNA

E. coli LE392 was infected with the phage. After 8 hours, the phage particles were collected. Then, the phage DNA was separated by treatment with proteinase K and phenol, followed by ethanol precipitation, according to the procedure described by Grossberger (Grossberger, D., Nucleic Acids. Res. 15: 6737, 1987).

(3) Subcloning of Target Gene

The four types of phage DNA were incised with Sal I, and electrophoresed through agarose.

The DNA was transferred onto a nylon membrane according to the procedure described by Southern (Southern, E. M., J. Mol. Biol. 98: 503–517, 1975), and hybridized under the same conditions as in the plaque hybridization in (1) above, using a probe of about 750 bp. A DNA fragment comprising the 5.2 kbp target gene was detected. The four phage DNA samples contained Sal I fragments of an identical size.

The 5.2 kbp DNA fragment was separated by using Sephaglass Band Prep Kit (Pharmacia Biotech), and subcloned to the Sal I site of plasmid pUC119, using the E. coli JM109 strain, to obtain plasmid pNCE4Sal.

Example A6

DNA Sequencing (1) Procedure for Genome DNA Sequencing

The genome DNA was sequenced on A. L. F. DNA Sequencer II (Pharmacia Biotech), using an acrylamide carrier available as Ready Mix Gel (Pharmacia Biotech) or Hydrolink Long Ranger (FMC) as sequencing gel. For gel preparation, A.L.F. grade reagents (N,N,N',N'-tetramethylethylenediamine, urea, and ammonium persulfate, Pharmacia Biotech) were used. For sequencing reactions, Autoread Sequencing Kit (Pharmacia Biotech) was used. The conditions for gel preparation, reaction and electrophoresis were selected according to the instructions in the supplied manuals.

The pNCE4Sal DNA fragment used as a template was denatured in alkali, using 10 µg of 2 M sodium peroxide, then annealed with the universal primer supplied with the Autoread Sequencing Kit for elongation. By analyzing the obtained sample with the sequencer, the nucleotide sequence was determined in a 546 bp region. Based on this sequence, a primer for FITC label sequencing was prepared (MNEG01), and allowed to react with pNCE4Sal for sequencing of the remaining regions. The obtained sequence, in turn, was used to prepare a primer for a next step of sequencing. The same procedure was repeated until the entire sequence of NCE4 was determined. The sequences of the primers used for FITC label sequencing were as follows:
MNEG-01: 5'-GTGATGAGGGCTGGCGACAGGCC-3'SEQ ID NO. 14 (19-mer)
MNEG-02: 5'-CTGCCACCTCTATTGCCGGCAGC-3'SEQ ID NO. 15 (23-mer)
MNEG-03: 5'-CCCGACGCCCTCAAGCCCGGCTG-3'SEQ ID NO. 16 (23-mer)
MNEG-04: 5'-GGCTGGAGCGGCTGCACCACCTG-3'SEQ ID NO. 17 (23-mer)
(2) Determination of Nucleotide Sequence Based on the result in (1) above, DNA fragments for use as primers in FITC label sequencing were prepared (MNEG-05 through MNEG-08) as follows:
MNEG-05: 5'-GACCTGACGGAAGCTGAAGCTCG-3'SEQ ID NO. 18 (23-mer)
MNEG-06: 5'-AGCAGTGCAGCCGCTGGGAGTCG-3'SEQ ID NO. 19 (23-mer)

MNEG-07: 5'-TGGCAGATGAGGACGTGGTGTTG-3'SEQ ID NO. 20 (23-mer)

MNEG-08: 5'-CGCAGCCGGACTTGGCGTCGAAG-3'SEQ ID NO. 21 (23-mer)

These primers were allowed to react with pNCE4Sal, using the Autoread Sequencing Kit. In the procedure, a 10 µg sample of the plasmid was denatured in alkali, then annealed with the primers, and allowed to react in the presence of T7 polymerase. As a result, the nucleotide sequence in a 1257 bp region of the Sal I fragment was determined as shown in SEQ ID No. 3.

Example A7

Analysis for Intron

In order to analyze the DNA for any intron, mRNA was first obtained from *Humicola insolens* MN200-1. Then, cDNA was prepared from the mRNA, using reverse transcriptase. Then, the sequence of the cDNA was compared with that of the genome DNA to determine the intron.

(1) Separation of RNA

*Humicola insolens* MN200-1 was incubated in a cellulase-inducing medium, preferably medium (N) as described earlier, for two days. The cells were recovered by centrifugation at 3500 rpm for 10 minutes. A 2 g sample of the cells was washed in sterilized water and, frozen with liquid nitrogen, and crushed using a blender (Nippon Seiki homogenizer AM-3). The homogenate was suspended in 10 ml of denaturing solution containing 4 M guanidine thiocyanate (4 M guanidine thiocyanate, 25 mM trisodium citrate, 0.5% N-sodium lauryl sarcosinate and 0.1 M mercaptoethanol). After agitation at room temperature for a few minutes at room temperature, the solution was neutralized with 1 ml of 2 M sodium acetate (pH 4.5), mixed with 10 ml of TE saturated phenol, then agitated carefully again. Then, after a 2 ml mixture of chloroform and isoamyl alcohol (24:1) was added, the solution was carefully agitated and centrifuged at 3500 rpm for 10 minutes to remove the cell body fraction which has been denatured with phenol. The supernatant (soluble fraction) was pipetted out and mixed with 10 ml of isopropanol to precipitate the nucleic acids. The precipitate was centrifuged at 3500 rpm for 10 minutes. The recovered nucleic acid was centrifuged again to wash in 70% aqueous solution of ethanol.

The resultant precipitate was dissolved in 3.5 ml of TE, and mixed with 880 µl of 10 M lithium chloride solution. After cooled at 5° C. for 2 hours, the mixture was centrifuged at 12000 rpm for 10 minutes. The resultant precipitate was recovered as the RNA fraction, and washed in 70% ethanol. The quantity and yield of the RNA fraction were 2.7 mg and 0.14%, respectively.

(2) Preparation of Poly-A Tail⁺ RNA (=mRNA)

The mRNA was prepared by using an mRNA purification kit (Pharmacia Biotech) as follows:

First, 1 mg of the RNA sample prepared in (1) above was dissolved in 1 ml of elution buffer, and denatured by heating at 65° C. for 10 minutes. After cooling the solution quickly in ice, 0.2 ml of sample buffer was added. The entire RNA solution was placed in an oligo-(dT) cellulose column, washed three times each with high salt and low salt buffers, and eluted using elution buffer heated to 65° C. The elution cycle was repeated again to obtain the mRNA fraction. The quantity and yield of the mRNA fraction were 19.2 µg and 2%, respectively.

(3) Preparation of cDNA

The cDNA was prepared by using Time Saver cDNA preparation kit (Pharmacia Biotech) as follows:

First, 5 µg of mRNA was dissolved in 20 µl of sample buffer. After heated at 65° C. for 10 minutes, the solution was added to first strand synthesis mix together with dithiothreitol solution and oligo-(dT) primer, and allowed to react at 37° C. for 1 hour. Then, the entire mixture was added to second strand mix, and allowed to react at 12° C. for 30 minutes, then at 22° C. for 1 hour, to obtain cDNA.

(4) Amplification of cDNA of Cellulase NCE4 by PCR

Using a 1 µg sample of the cDNA prepared as described above as a template, the target cDNA was selectively amplified by PCR. Oligonucleotide primers with the following sequences were prepared for use as primers for the N- and C-terminals:

NCE4-CN: 5'-ATGCGTTCCTCCCCTCTCCTCCGC-TCCGCC-3'SEQ ID NO. 22 (30-mer)

NCE4-CC: 5'-TACAGGCACTGATGGTACCAG-TCATTAATC-3'SEQ ID NO. 23 (30-mer).

The procedure for PCR was as follows:

First, 1 µM each of primers per 1 µg of *Humicola insolens* cDNA were added. After denatured by heating at 94° C. for 10 minutes in the presence of dNTP, the DNA was mixed with Taq polymerase (recombinant Taq, Takara Shuzo). Then, the DNA was amplified through 30 cycles of reactions at 94° C. for 1 minute, at 50° C. for 2 minutes, and at 72° C. for 3 minutes. The result of agarose gel electrophoresis showed that the length of the amplified fragment was 0.9 kbp. The fragment was then concentrated by ethanol precipitation, and cloned using pT7 Blue T vector kit (Novagen) to obtain plasmid pCNCE4.

(5) Nucleotide Sequencing of cDNA

The cDNA was sequenced by using the Autoread Sequencing Kit as in the foregoing procedure. The plasmid pCNCE4 was denatured with alkali, using 2 M sodium peroxide, then precipitated in ethanol. Using this single-stranded plasmid as a template, the DNA was allowed to react in the presence of T7 polymerase. Then, using the aforementioned synthetic primers MNEGO1, MNEGO2, MNEGO3, MNEGO4, MNEGO5, MNEGO6, MNEGO7 and MNEGO8, as well as the universal primer supplied with the kit and the reverse primer, the cDNA was sequenced.

The result revealed that there was one intron of 56 bp. In the sequence of SEQ ID No. 3, the sequences at the beginning and end of the non-translated region, and the regulatory sequence within the intron were as follows (numerals correspond to the amino acid numbers in SEQ ID No. 3):

Intron: 453 to 458, 506 to 508, and 491 to 497

Example B1

Construction of Plasmid pMKD01

(1) Preparation of Plasmid pUC118BN

A 1 µg sample of pUC118 DNA was incised with BamH I, and treated with phenol to deactivate the restriction enzyme. After ethanol precipitation, the sample was dissolved in a small amount of TE buffer (10 mM Tris-HCl (pH 8.0), and 1 mM EDTA). The DNA was blunted using a DNA blunting kit (Takara Shuzo), then ligated using a DNA ligation kit (Takara Shuzo) to a cyclic form. The ligated mixture was introduced in *E. coli* competent cells JM109

(Takara Shuzo). The resultant transformants were incubated on LB agar medium (1% polypepton, 0.5% yeast extract, 1% NaCl, and 1.5% agar) containing 100 μg/ml of ampicillin, 1 mM of IPTG and 0.004% of X-gal. Only those transformants which grew to form white colonies were selected. These transformants were then incubated overnight at 37° C. on LB medium (1% polypepton, 0.5% yeast extract, 1% NaCl) containing 100 μg/ml of ampicillin. The plasmid DNA was recovered from the culture by alkali-SDS. This plasmid DNA was incised with BamH I, then electrophoresed through 0.8% agarose gel. The plasmid DNA in which the BamH I site of the pUC118 DNA was thus destroyed was selected. This plasmid was designed as pUC118BN.

(2) Construction of Plasmid pUC118BSN

A 1 μg sample of pUC118BN DNA was incised with Sph I. Then, according to the same procedure as above, plasmid DNA in which the Sph I site of pUC118BN was destroyed was selected as pUC118BSN.

(3) Construction of Plasmid pM21

(A) Isolation of Cellulase NCE2 Gene

A Pst I-Xba I fragment with a total length of 3.4 kbp, comprising the cellulase NCE2 gene and a 1.4 kbp promoter sequence and a 0.5 kbp terminator sequence on the upstream and downstream regions of the gene, respectively, was obtained from *Humicola insolens* according to the procedure disclosed in Japanese Patent Laid-Open No. 8-126492. Then, the fragment was ligated with the Pst I-Xba I site of the plasmid DNA pUC118BSN to obtain plasmid DNA pUC118BSN-PX.

(B) Site-specific mutation of plasmid pUC118BSN-PX

A BamH I site was introduced by site-specific mutation on the downstream side of the N-terminal of the NCE2 gene, and on the immediate downstream side of the termination codon of the gene, in the following manner: *E. coli* JM 109 strain was transformed with the plasmid pUC118BSN-PX, then infected with the helper phage M13KO7. The mutant was incubated in 30 ml of 2xYT liquid medium (1.6% bactotryptone, 0.8% yeast extract and 0.5% NaCl) containing 150 μg/ml of ampicillin and 70 μg/ml of kanamycin at 37° C. for 16 to 20 hours. From the resultant supernatant, M13 single-stranded DNA (ssDNA) was recovered. Site-specific mutation was introduced in the ssDNA, using two types of synthetic oligonucleotides and Scultper In Vitro Mutagenesis System (Amersham). The sequences of the synthetic oligonucleotides used as primers were as follows:

MNC-02: 5'-GAGCGCCAGAACTGTGGATCCACTT-GGTGAGCAATG-3'SEQ ID NO. 24 (36-mer)

MNC-03: 5'-TCCGCCGTTCTGAGCGGATCCAGGCG-TTTGGCGCG-3'SEQ ID NO. 25 (35-mer)

After the site-specific mutation, the DNA was introduced in *E. coli* TG1. The transformant was then incubated in an LB medium (1% polypepton, 0.5% yeast extract and 1% NaCl) containing 100 μg/ml of ampicillin. The recovered plasmid DNA was incised with BamH I, and electrophoresed through 0.8% agarose gel, to select the plasmid DNA pUC118BSN-PX in which two BamH I sites had been introduced (plasmid DNA pM21).

(4) Isolation of Cellulase NCE3 Gene

Based on the sequence of a known cellobiohydrolase gene derived from *Humicola grisea* (de Oliviera Alzevedo, M., et al., J. General Microbiol., 136: 2569–2576, 1990), a cellobiohydrolase gene derived from *Humicola insolens* (NCE3) was isolated by PCR in the following manner:

(A) Isolation of Genome DNA

The genome DNA of *Humicola insolens* MN200-1 was obtained according to the procedure described in Example A3.

(B) Amplification of Cellulase NCE3 Gene by PCR

Based on the sequence of the cellobiohydrolase gene derived from Humicola grisea, the NCE3 gene of *Humicola insolens* was isolated by PCR. In order to allow the PCR product containing the NCE3 gene to be ligated at the BamHI site of the plasmid pM21 with frame aligned, primers containing a BamHI site were constructed. The sequences of the synthetic oligonucleotides used as primers were as follows:

MKA-05: 5'-GCCGCCCAGCAGGCGGGATCCCTCA-CCACCGAGAGG-3'SEQ ID NO. 26 (36-mer)

MKA-06: 5'-TGATCGTCGAGTCAGGGATCCAGAA-TTTACAGGCAC-3'SEQ ID NO. 27 (36-mer)

The PCR was performed according to the instructions provided with the LA PCR Kit Ver. 2 (Takara Shuzo) as follows:

First, 1 μM each of the primers, 400 μM of dNTP, and 2.5 U of LA Taq polymerase were added per 1 μg of *Humicola insolens* genome DNA, which had been obtained as described above. The DNA was then amplified through 30 cycles of reactions at 94° C. for 1 minute, at 55° C. for 2 minutes, and at 72° C. for 3 minutes. The result of 0.8% agarose gel electrophoresis showed that a 1.6 kbp DNA fragment was amplified. The DNA fragment was recovered by using Sephaglass Band Prep Kit (Pharmacia Biotech), and ligated with pT7 Blue T vector kit (Novagen) to obtain plasmid DNA pK21.

(5) Construction of plasmid pKM04

The plasmid pK21 DNA was digested with BamH I, and a 1.6 kbp DNA fragment was recovered. Furthermore, the plasmid pM21 DNA was digested with BamH I, and heated at 70° C. for 10 minutes to deactivate the restriction enzyme. Then, the DNA was dephosphorylated with alkali phosphatase derived from calf (Takara Shuzo). Finally, the DNA was electrophoresed through 0.8% agarose gel, and a 5.2 kbp DNA fragment was recovered. The 1.6 kbp DNA fragment derived from pK21 and the 5.2 kbp DNA fragment derived from pM21 were ligated to obtain plasmid pKM04.

(6) Preparation of plasmid pMKD01

First, the destmycin-resistant gene disclosed in Japanese Patent Laid-Open No.59-175889 was transformed so that it can be expressed in *Humicola insolens*, using the promoter and terminator of the trp C gene derived from *Aspergillus nidulans*, according to a known procedure (Mullaney, E. J. et al., Mol. Gen. Genet.199: 37–45, 1985). The mutant gene was introduced in the Xba I site of the plasmid pKM04 to obtain plasmid pMKD01.

Example B2

Transformation of *Humicola insolens* Using Plasmid pMKD01

(1) Preparation of High-Purity Sample of Plasmid pMKD01

In order to introduce the plasmid pMKD01 into *Humicola insolens*, a high-purity sample of pMKD01 was prepared as follows:

*E. coli* JM109 was transformed with the plasmid pMKD01, and incubated overnight in 100 ml of LB medium containing 100 μg/ml of ampicillin at 37° C. The culture was then purified by using FlexiPrep Kit (Pharmacia Biotech) to obtain 1 μg/μl of pMKD01 plasmid DNA.

(2) Transformation of *Humicola insolens*

*Humicola insolens* MN200-1 was incubated in medium (S) at 37° C. After 24 hours, the cells were collected by centrifugation at 3000 rpm for 10 minutes. The composition of medium (S) was the same as that of medium (N) described earlier, except that it contained 3.0% glucose but no avisel. The obtained cells were washed in 0.5 M sucrose, and suspended in 10 ml of cellulase solution (5 mg/ml Novozyme 234 (NLI), 5 mg/ml Cellulase Onozuka R-10 (Yakult) and 0.5 M sucrose) which had been filtrated through a 0.45 µm filter. After the suspension was shaken at 30° C. for 60 to 90 minutes, the hyphae were cellulated. The resultant protoplasts were recovered from the suspension by filtration, followed by centrifugation at 2500 rpm for 10 minutes, then washed in SUTC buffer (0.5 M sucrose, 10 mM calcium chloride and 10 mM Tris-HCl (pH 7.5)).

The protoplasts were then suspended in 1 ml of SUTC buffer, and mixed with 10 µg of DNA (TE) solution (10 µl) per 100 µl of suspension, then iced still for 5 minutes. Then, the suspension was mixed with 400 µl of PEG solution (60% PEG4000, 10 mM calcium chloride and 10 mM Tris-HCl (pH 7.5)), and iced still again for 20 minutes. After 10 ml of SUTC buffer was added, the mixture was centrifuged at 2500 rpm for 10 minutes. The protoplasts thus recovered was suspended in 1 ml of SUTC buffer, and centrifuged again at 4000 rpm for 5 minutes, then suspended in 100 µl of SUTC buffer.

The obtained protoplast suspension was applied to a YMG medium (1% glucose, 0.4% yeast extract, 0.2% malt extract and 1% agar (pH 6.8)) containing 200 µg/ml of hygromycin B, together with YMG soft agar, and incubated at 37° C. for five days. The resultant colonies were selected as transformants.

(3) Incubation and SDS-PAGE Analysis of pMKD01 Transformants

From the culture of *Humicola insolens* MN200-1, which had been transformed with plasmid pMKD01, 50 strains which exhibited hygromycin resistance were selected. These strains were incubated in medium (N) at 37° C. for 5 days. The supernatant was analyzed by SDS-PAGE, the protein band corresponding apparently to NCE3 was three to four times stronger in five of the clones of the pMKD01 transformants than in the original strain.

(4) Amino Acid Sequencing on N-terminal of Recombinant NCE3

In order to confirm that the strengthened protein band as found in SDS-PAGE was derived from the NCE3 gene, the amino acid sequence on the N-terminal of this protein was determined as follows: The supernatant of the cultures of the original strain and the strain which exhibited strengthened NCE3 expression was analyzed by column chromatography using the FPLC system according to the procedure described in Example A2. Then, the peak that was characteristically higher in the strain which exhibited strengthened NCE3 expression than in the original strain was collected and freeze-dried. This protein sample was then dissolved in a small amount of water, and electrophoresed using 8% Gel SDS-PAGE mini (Difco). After the protein sample was transferred electrically onto a PVDF membrane according to the procedure described in Example A2, it was stained with Comazy brilliant blue R-250, decolored, then washed in water. The region blotted with a protein with a molecular weight of 66 kD was cut out. The modification residues on the N-terminal of the protein were removed according to the procedure described by Podell, D. N., et al. (Podell, D. N. et al., Biochem. Biophys. Res. Commun., 81: 176, 1978). The target protein was cut out, and maintained at 37° C. for 30 minutes with a small amount of 0.5% polyvinyl pyrrolidone (molecular weight =40,000; Sigma) in 100 mM acetic acid solution, then washed carefully in water. Then, after the modification residues on the N-terminal were removed with Pfu pyroglutamic acid aminopeptidase (Takara Shuzo), the protein was washed in water and dried in air. Finally, the protein was sequenced by using the protein sequencer Model 492 to determine the sequence of the 15 amino acids on the N-terminal. The determined amino acid sequence was as follows:

Amino acid sequence on N-terminal: Asn-Cys-Gly-Ser-Leu-Thr-Thr-Glu-Arg-His-Pro-Ser-Leu-Ser-Trp (15 amino acids; amino acids 2–16 of SEQ ID NO 4).

As a result, the amino acid sequence on the N-terminal proved to be identical to the presumed amino acid sequence of the protein fused with cellulase NCE2 and NCE3 as inferred from the nucleotide sequence of the plasmid pMKD01.

(5) FPLC Analysis of pMKD01 Transformant

The supernatant of the cultures of the five clones which exhibited strengthened expression of NCE3, as found in SDS-PAGE, was further analyzed quantitatively by column chromatography, using the FPLC system under the same conditions as in (4) above. The NCE3 peak was collected and freeze-dried, then weighed to compare the productivity between the transformant which exhibited strengthened expression and the original strain. The result was as follows:

TABLE 1

| Production of NCE3* | |
|---|---|
| *Humicola insolens* MN200-1 (original strain) | 0.46 g |
| *Humicola insolens* pMKD01 | 1.8 g |

Example B3

Preparation of Plasmid pEGD01

After digested with BamH I, the plasmid pMKD01 was heated at 70° C. to deactivate the restriction enzyme, then dephosphorylated. As a result, a 8.2 kbp DNA fragment was recovered.

Then, based on the sequence of the NCE4 gene derived from *Humicola insolens*, which had been obtained in Examples A1 through A7, the NCE4 gene was amplified by PCR. In order to allow the PCR product containing the NCE4 gene to be ligated with the 8.2 kbp BamH I fragment of the plasmid pMKD01 with frame aligned, primers containing a BamH I site were constructed. The sequences of the synthetic oligonucleotides used as primers were as follows:

NCE4-N: 5'-CCGGTGTTGGCCGGATCCGCTGAT-GGCAAG-3'SEQ ID NO. 28 (30-mer)
NCE4-C: 5'-TAAGGCCCTCAAGGATCCCTGCGT-CTACAG-3'SEQ ID NO. 29 (30-mer)

The PCR was performed as follows: First, 1 µM each of the primers, 400 µM of dNTP, and 2.5 U of Pfu DNA polymerase (Stratagene) were added per 1 µg of *Humicola insolens* genome DNA. Then the 0.8 kbp DNA fragment was amplified through 25 cycles of reactions at 94° C. for 1 minute, at 55° C. for 2 minutes, and at 72° C. for 3 minutes. The 0.8 kbp DNA fragment was recovered and ligated with the 8.2 kbp BamH I fragment of pMKD01 to obtain plasmid DNA pEGD01.

Example B4

Expression of Plasmid pEGD1

(1) Transformation of *Humicola insolens* with plasmid pEGD01

*Humicola insolens* MN200-1 was transformed with the plasmid pEGD01 according to the procedure described in Example B2. First, a high-purity sample of pEGD01 was prepared to obtain a 1 µg/µl sample of pEGD01 plasmid DNA. Using 10 1 of this pEGD01 solution, the *Humicola insolens* MN200-1 strain was transformed. From the culture, 50 strains which exhibited hygromycin resistance were selected. These transformants were incubated in medium (N) at 37° C. for 5 days. When the supernatant was analyzed by SDS-PAGE, the protein band corresponding apparently to NCE4 was 10 to 16 times stronger in ten of the clones of the pEGD01 transformants than in the original strain.

(2) Amino Acid Sequencing on N-terminal of Recombinant NCE4

In order to confirm that the strengthened protein band as found in SDS-PAGE was derived from the NCE4 gene, the amino acid sequence on the N-terminal of this protein was determined as follows: First, the supernatant of the cultures of the original strain and the strain which exhibited strengthened NCE4 expression was analyzed by column chromatography using the FPLC system according to the procedure described in Example B2. Then, the peak that was characteristically higher in the strain which exhibited strengthened NCE4 expression than in the original strain was collected and freeze-dried. After this protein sample was dissolved in a small amount of water, the modification residues on the N-terminal were removed according to the procedure described in Example B2. The amino acid sequence on the N-terminal was determined using the same protein sequencer as in the foregoing procedure. Two amino acid sequences were found on the N-terminal as shown below at a ratio of about 7:3. Similarly, without removing the modification residues on the N-terminal, the amino acid sequence on the N-terminal was determined using the same protein sequencer. Only amino acid sequence 1 as shown below was found.

Amino acid sequence 1 on N-terminal: Val-Val-Glu-Glu-Arg-Gln-Asn-Cys-Gly -Ser-Ala-Asp-Gly-Lys-Ser-Thr-Arg-Tyr-Trp-Asp SEQ ID NO. 5 (20 amino acids)

Amino acid sequence 2 on N-terminal: Asn-(Cys)-Gly-Ser-Ala-Asp-Gly-Lys-Ser -Thr-Arg-Tyr-Trp-Asp-(Cys)-(Cys)-Lys-Pro-Ser-(Cys) (20 amino acids; amino acids 2–21 of SEQ ID NO 6)

As a result, the amino acid sequence on the N-terminal proved to be identical to the presumed amino acid sequence of the protein fused with cellulase NCE2 and NCE4 as inferred from the nucleotide sequence of the plasmid pEGD01. Furthermore, the fact that two amino acid sequences were found on the N-terminal indicated that, when the signal sequence of the fused protein was incised, it was processed at more than one point.

(3) FPLC Analysis of Transformant with pEGD01

The supernatant of the cultures of the five clones which exhibited strengthened expression of NCE4 as found in SDS-PAGE was further analyzed quantitatively by column chromatography using the FPLC system. The NCE4 peak was collected and freeze-dried, then weighed to compare the productivity between the transformant which exhibited strengthened expression and the original strain. The result was as follows:

TABLE 2

| Production of NCE4* | |
|---|---|
| *Humicola insolens* MN200-1 (original strain) | 0.28 g |
| *Humicola insolens* PEGD01 | 4.5 g |

*production per one liter of culture.

Example B5

Preparation of Plasmid pIED02

(1) Preparation of plasmid pID01

The plasmid pEGD01 was digested with Hind III and BamH I, and a 7.2 kbp DNA fragment was recovered.

Then, based on the sequence of the NCE1 gene derived from Humicola insolens, which had been obtained according to the procedure disclosed in Japanese Patent Laid-Open No. 8-5663, the DNA fragment corresponding to the promoter and signal sequence of the NCE1 gene was amplified by PCR. In order to allow the PCR product containing the promoter and signal sequence of the NCE1 gene to be ligated with the 7.2 kbp Hind III-BamHI fragment of the plasmid pEGD01, primers containing a HindIII site and a BamHI site were constructed. The sequences of the synthetic oligonucleotides used as primers were as follows:

PNCE1-N: 5'-GTCATGAAGCTTCATTAAGGTACGT-ATGCAAC-3'SEQ ID NO. 30 (32-mer)

PNCE1-C: 5'-GGTGATGGATCCGGCCTGCTGGGCA-GCGACGC-3'SEQ ID NO. 31 (32-mer)

The PCR was performed in a similar manner to Example 3 as follow: First, 1 µM each of the primers, 400 µM of dNTP, and 2.5 U of Pfu DNA polymerase were added per 1 µg of *Humicola insolens* genome DNA. The 1.5 kbp DNA fragment was amplified through 23 cycles of reactions at 94° C. for 1 minute, at 55° C. for 2 minutes, and at 72° C. for 4 minutes. The PCR product was digested with Hind III and BamH I. The recovered 1.5 kbp DNA fragment was ligated with the 7.2 kbp Hind III-BamH I fragment of pEGD01 to obtain plasmid DNA pID01.

(2) Preparation of Plasmid pIED02

The plasmid pID01 was digested with BamH I, then heated at 70° C. to deactivate the restriction enzyme. After dephosphorylation, an 8.6 kbp DNA fragment was recovered. Further, the plasmid pEGD01 was digested with BamH I, and a 0.8 kbp DNA fragment containing the NCE4 gene was recovered. These two fragments were ligated to obtain plasmid pIED02.

Example B6

Expression of Plasmid pIED02

(1) Transformation of *Humicola insolens* with plasmid pIED02

*Humicola insolens* MN200-1 was transformed with the plasmid pIED02 according to the procedure described in Example B2 as follows: First, a high-purity sample of pIED02 was prepared to obtain 1 µg/µl of pIED02 plasmid DNA. Using 10 µl of this pIED02 solution, the *Humicola insolens* MN200-1 strain was transformed. From the culture, 50 strains which exhibited hygromycin resistance were selected. These transformants were incubated in medium (N) at 37° C. for 5 days. When the supernatant was analyzed by SDS-PAGE, the protein band corresponding apparently to NCE4 was 5 to 10 times stronger in five of the clones of the pIED02 transformants than in the original strain.

(2) Amino Acid Sequencing on N-terminal of Recombinant NCE4

In order to confirm that the strengthened protein band as found in SDS-PAGE was derived from the NCE4 gene, the amino acid sequence on the N-terminal of this protein was determined as follows. First, the supernatant of the cultures of the original strain and the strain which exhibited strengthened NCE4 expression was analyzed by column chromatography using the FPLC system according to the procedure described in Example B2. Then, the NCE4 peak was collected and freeze-dried. After this protein sample was dissolved in a small amount of water, the modification residues on the N-terminal were removed according to the procedure described in Example B2. Finally, the protein was sequenced by using the same protein sequencer as in the foregoing procedure to determine the sequence of the 15 amino acids on the N-terminal. The determined amino acid sequence was as follows:

Amino acid sequence on N-terminal: Gln-Ala-Gly-Ser-Ala-Asp-Gly-Lys-Ser-Thr -Arg-Tyr-Trp-Asp-(Cys) (15 amino acids; amino acids 2–16 of SEQ ID NO. 7)

As a result, the amino acid sequence on the N-terminal proved to be identical to the presumed amino acid sequence of the protein fused with cellulase NCE1 and NCE4 as inferred from the nucleotide sequence of the plasmid pIED02.

(3) FPLC Analysis of Transformant with pIED02

The supernatant of the cultures of the five clones which exhibited strengthened expression of NCE4 as found in SDS-PAGE was further analyzed quantitatively by column chromatography using the FPLC system. The NCE4 peak was collected and freeze-dried, then weighed to compare the productivity between the transformant which exhibited strengthened expression and the original strain. The result was as follows:

TABLE 3

Production of NCE4*

| | |
|---|---|
| Humicola insolens MN200-1 (original strain) | 0.28 g |
| Humicola insolens pIED02 | 2.9 g |

*production per one liter of culture.

What is claimed is:

1. An isolated protein obtained by the following steps:
    transforming a Humicola microorganism with the expression vector pMKD01, pEGD01, or pIED02,
    incubating the transformed microorganism in a culture, and
    isolating said protein encoded with the expression vector from the culture, wherein said protein comprises in the N terminal of the protein an amino acid sequence selected from the group consisting of: SEQ ID NO: 4, SEQ ID NO: 5, SEQ ID NO: 6 and SEQ ID NO: 7.

2. An isolated protein having SEQ ID NO: 4 in the N terminal of the protein, wherein said protein is obtained by culturing a Humicola microorganism transformed with the expression vector pMKD01.

3. An isolated protein having SEQ ID NO: 5 or SEQ ID NO: 6 in the N terminal of the protein, wherein said protein is obtained by culturing a Humicola microorganism transformed with the expression vector pEGD01.

4. An isolated protein having SEQ ID NO: 7 in the N terminal of the protein, wherein said protein is obtained by culturing a Humicola microorganism transformed with the expression vector pIED02.

* * * * *